United States Patent
Samsonov et al.

(10) Patent No.: US 9,493,777 B1
(45) Date of Patent: Nov. 15, 2016

(54) METHOD FOR PRODUCING AN L-AMINO ACID USING A BACTERIUM OF THE FAMILY ENTEROBACTERIACEAE HAVING OVEREXPRESSED THE YAJL GENE

(71) Applicant: AJINOMOTO CO., INC., Tokyo (JP)

(72) Inventors: Valery Vasilievich Samsonov, Moscow (RU); Natalia Sergeevna Eremina, Moscow (RU); Natalia Viktorovna Stoynova, Moscow (RU); Vera Georgievna Doroshenko, Moscow (RU)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 15/233,258

(22) Filed: Aug. 10, 2016

Related U.S. Application Data

(63) Continuation of application No. PCT/JP2015/054508, filed on Feb. 12, 2015.

(30) Foreign Application Priority Data

Feb. 14, 2014 (RU) ................................ 2014105547

(51) Int. Cl.
| | |
|---|---|
| C12P 13/22 | (2006.01) |
| C12N 15/70 | (2006.01) |
| C12P 13/08 | (2006.01) |
| C12P 13/10 | (2006.01) |
| C12P 13/12 | (2006.01) |
| C12P 13/14 | (2006.01) |
| C12P 13/06 | (2006.01) |
| C12P 13/24 | (2006.01) |

(52) U.S. Cl.
CPC ............... *C12N 15/70* (2013.01); *C12P 13/06* (2013.01); *C12P 13/08* (2013.01); *C12P 13/10* (2013.01); *C12P 13/12* (2013.01); *C12P 13/14* (2013.01); *C12P 13/222* (2013.01); *C12P 13/227* (2013.01); *C12P 13/24* (2013.01)

(58) Field of Classification Search
CPC ......... C12P 13/04; C12P 13/10; C12P 13/14; C12P 13/24
USPC ........................................................ 435/108
See application file for complete search history.

(56) References Cited

U.S. PATENT DOCUMENTS

| | | |
|---|---|---|
| 4,278,765 A | 7/1981 | Debabov et al. |
| 4,346,170 A | 8/1982 | Sano et al. |
| 5,661,012 A | 8/1997 | Sano et al. |
| 5,965,391 A | 10/1999 | Reinscheid et al. |
| 5,998,178 A | 12/1999 | Hashiguchi et al. |
| 6,040,160 A | 3/2000 | Kojima et al. |
| 8,394,612 B2 | 3/2013 | Imaizumi et al. |
| 8,460,903 B2 | 6/2013 | Savrasova et al. |
| 8,679,798 B2 | 3/2014 | Yampolskaya et al. |
| 8,728,774 B2 | 5/2014 | Rybak et al. |
| 8,785,161 B2 | 7/2014 | Rybak et al. |
| 8,852,897 B2 | 10/2014 | Savrasova et al. |
| 9,175,319 B2 | 11/2015 | Stoynova et al. |
| 9,279,137 B2 | 3/2016 | Sycheva et al. |
| 2006/0216796 A1 | 9/2006 | Hashiguchi et al. |
| 2009/0087887 A1 | 4/2009 | Kataoka et al. |
| 2009/0137010 A1 | 5/2009 | Shakulov et al. |
| 2012/0237986 A1 | 9/2012 | Ziyatdinov et al. |
| 2015/0017693 A1 | 1/2015 | Sycheva et al. |

FOREIGN PATENT DOCUMENTS

| | | |
|---|---|---|
| EP | 0685555 | 12/1995 |
| WO | WO95/16042 | 6/1995 |
| WO | WO96/15246 | 5/1996 |
| WO | WO2007/116955 | 10/2007 |

OTHER PUBLICATIONS

U.S. Appl. No. 15/082,274, Kuvaeva et al., filed Mar. 28, 2016.
U.S. Appl. No. 15/097,632, Hook et al., filed Apr. 13, 2016.
U.S. Appl. No. 15/165,606, Sansonov et al., filed May 26, 2016.
U.S. Appl. No. 15/164,637, Shakulov et al., May 25, 2016
Kthiri, F., et al., "Protein Aggregation in a Mutant Deficient in YajL, the Bacterial Homolog of the Parkinsonism-associated Protein DJ-1," J. Biol. Chem. 2010;285(14):10328-10336.
Messaoudi, N., et al., "Global Stress Response in a Prokaryotic Model of DJ-1-Associated Parkinsonism," J. Bacteriol. 2013;195(6):1167-1178.
Wilson, M. A., et al., "The Atomic Resolution Crystal Structure of the YajL (ThiJ) Protein from *Escherichia coli*: A Close Prokaryotic Homologue of the Parkinsonism-associated Protein DJ-1," J. Mol. Biol. 2005;353:678-691.
International Search Report for PCT Patent App. No. PCT/JP2015/054508 (Jun. 3, 2015).
Written Opinion for PCT Patent App. No. PCT/JP2015/054508 (Jun. 3, 2015).

*Primary Examiner* — Tekchand Saidha

(74) *Attorney, Agent, or Firm* — Shelly Guest Cermak; Cermak Nakajima & McGowan LLP

(57) ABSTRACT

The present invention provides a method for producing L-amino acids or salts thereof by fermentation using a bacterium of the family Enterobacteriaceae, particularly a bacterium belonging to the genus *Escherichia*, which has been modified to overexpress the yajL gene.

8 Claims, No Drawings

METHOD FOR PRODUCING AN L-AMINO ACID USING A BACTERIUM OF THE FAMILY ENTEROBACTERIACEAE HAVING OVEREXPRESSED THE YAJL GENE

This application is a Continuation of, and claims priority under 35 U.S.C. §120 to, International Application No. PCT/JP2015/054508, filed Feb. 12, 2015, and claims priority therethrough under 35 U.S.C. §119 to Russian Patent Application No. 2014105547, filed Feb. 14, 2014, the entireties of which are incorporated by reference herein. Also, the Sequence Listing filed electronically herewith is hereby incorporated by reference (File name: 2016-08-10T_US-529_Seq_List; File size: 12 KB; Date recorded: Aug. 10, 2016).

BACKGROUND OF THE INVENTION

Field of the Invention

The present invention relates to the microbiological industry, and specifically to a method for producing L-amino acids by fermentation of a bacterium of the family Enterobacteriaceae which has been modified to overexpress the yajL gene.

Brief Description of the Related Art

Conventionally, L-amino acids are industrially produced by fermentation methods utilizing strains of microorganisms obtained from natural sources, or mutants thereof. Typically, the microorganisms are modified to enhance production yields of L-amino acids.

Many techniques to enhance L-amino acids production yields have been reported, including transformation of microorganisms with recombinant DNA (see, for example, U.S. Pat. No. 4,278,765 A) and alteration of regulatory regions such as a promoter, leader sequence, and/or attenuator, or others known to the person skilled in the art (see, for example, US20060216796 A1 and WO9615246 A1). Other techniques for enhancing production yields include increasing the activities of enzymes involved in amino acid biosynthesis and/or desensitizing the target enzymes to the feedback inhibition by the resulting L-amino acid (see, for example, WO9516042 A1, EP0685555 A1 or U.S. Pat. Nos. 4,346,170 A, 5,661,012 A, and 6,040,160 A).

Another method for enhancing L-amino acid production yields is to attenuate expression of a gene or several genes which are involved in degradation of the target L-amino acid, genes which divert the precursors of the target L-amino acid from the L-amino acid biosynthetic pathway, genes involved in the redistribution of the carbon, nitrogen, and phosphate fluxes, and genes encoding toxins, etc.

The yajL gene encodes the YajL protein which belongs to the PfpI/Hsp31/DJ-1 superfamily that includes chaperones, peptidases, and the protein DJ-1 (Messaoudi N. et al., Global stress response in a prokaryotic model of DJ-1-associated Parkinsonism, *J. Bacteriol.*, 2013, 195(6):1167-1178). The YajL is the closest prokaryotic homolog of DJ-1. For example, the *Escherichia coli* (*E. coli*) YajL protein has 40% sequence identity and a similar three-dimensional structure with human DJ-1, an oncogene and neuroprotective protein whose loss-of-function mutants are associated with certain types of familial, autosomal recessive Parkinsonism (Wilson M. A. et al., The atomic resolution crystal structure of the YajL (ThiJ) protein from *Escherichia coli*: a close prokaryotic homologue of the Parkinsonism-associated protein DJ-1, *J. Mol. Biol.*, 2005, 353(3):678-691). The high homology and similarity of crystal structures of YajL and DJ-1 suggest that the proteins have similar function. It was found recently that YajL protects bacteria against oxidative stress and oxidative-stress-induced protein aggregation possibly through its chaperone function and control of gene expression (Kthiri F. et al., Protein aggregation in a mutant deficient in YajL, the bacterial homolog of the Parkinsonism-associated protein DJ-1, *J. Biol. Chem.*, 2010, 285: 10328-10336). In *E. coli*, YajL functions as a covalent chaperone that, upon oxidative stress, forms mixed disulfides with chaperones, proteases, ribosomal proteins, catalases, peroxidases, and FeS proteins (Messaoudi N. et al., *J. Bacteriol.*, 2013, 195(6):1167-1178).

Until now, no data has been reported demonstrating the effect from overexpression of the yajL gene on L-amino acid production by the modified bacterial strains of the family Enterobacteriaceae.

SUMMARY OF THE INVENTION

An aspect of the present invention is to provide a bacterium belonging to the family Enterobacteriaceae, which can belong to the genus *Escherichia* and, more specifically, to the species *Escherichia coli* (*E. coli*), which has been modified to overexpress the yajL gene.

Another aspect of the present invention is to provide a method for producing an L-amino acid such as L-alanine, L-arginine, L-asparagine, L-aspartic acid, L-citrulline, L-cysteine, L-glutamic acid, L-glutamine, glycine, L-histidine, L-isoleucine, L-leucine, L-lysine, L-methionine, L-ornithine, L-phenylalanine, L-proline, L-serine, L-threonine, L-tryptophan, L-tyrosine or L-valine using a bacterium of the family Enterobacteriaceae as described hereinafter.

These aims were achieved by the unexpected finding that overexpression of the yajL gene in a bacterium belonging to the family Enterobacteriaceae, which can belong to the genus *Escherichia* and, more specifically, to the species *E. coli*, confers on the microorganism higher productivity of L-amino acids such as, in particular, but not limited to, L-amino acids of the pyruvate family such as L-valine, and aromatic L-amino acids such as L-phenylalanine.

An aspect of the present invention is to provide a method for producing an L-amino acid comprising:

(i) cultivating an L-amino acid-producing bacterium of the family Enterobacteriaceae, in a culture medium to produce said L-amino acid in the bacterium or the culture medium, or both; and, (ii) collecting said L-amino acid from the bacterium or the culture medium, or both, wherein the bacterium has been modified to overexpress the yajL gene.

It is a further aspect of the present invention to provide the method as described above, wherein the bacterium belongs to the genus *Escherichia*.

It is a further aspect of the present invention to provide the method as described above, wherein the bacterium is *Escherichia coli*.

It is a further aspect of the present invention to provide the method as described above, wherein the yajL gene is overexpressed by increasing a copy number of the yajL gene or modifying an expression control sequence of the yajL gene so that the expression of the gene is enhanced as compared to a non-modified bacterium.

It is a further aspect of the present invention to provide the method as described above, wherein the L-amino acid is selected from the group consisting of L-phenylalanine, L-tryptophan, L-tyrosine, L-alanine, L-arginine, L-asparagine, L-aspartic acid, L-citrulline, L-cysteine, L-glutamic acid, L-glutamine, glycine, L-histidine, L-isoleucine, L-leucine, L-lysine, L-methionine, L-ornithine, L-proline, L-serine, L-threonine, and L-valine.

It is a further aspect of the present invention to provide the method as described above, wherein the L-amino acid is selected from the group consisting of L-alanine, L-isoleucine, L-leucine, L-valine and L-phenylalanine.

It is a further aspect of the present invention to provide the method as described above, wherein the L-amino acid is L-phenylalanine.

It is a further aspect of the present invention to provide the method as described above, wherein the L-amino acid is L-valine.

DESCRIPTION OF THE PREFERRED EMBODIMENTS

The present invention is described in detail below.

1. Bacterium

The phrase "an L-amino acid-producing bacterium" can mean a bacterium of the family Enterobacteriaceae which has an ability to produce, excrete or secrete, and/or cause accumulation of an L-amino acid in a culture medium or the bacterial cells when the bacterium is cultured in the medium.

The phrase "an L-amino acid-producing bacterium" can also mean a bacterium which is able to produce, excrete or secrete, and/or cause accumulation of an L-amino acid in a culture medium in an amount larger than a wild-type or parental strain, such as *E. coli* K-12, and can mean that the microorganism is able to cause accumulation in a medium of an amount not less than 0.5 g/L or not less than 1.0 g/L of the target L-amino acid.

The phrase "L-amino acid-producing ability" can mean the ability of the bacterium to produce, excrete or secrete, and/or cause accumulation of the L-amino acid in a medium or the bacterial cells to such a level that the L-amino acid can be collected from the medium or the bacterial cells, when the bacterium is cultured in the medium.

The phrase "L-amino acid" can mean L-alanine, L-arginine, L-asparagine, L-aspartic acid, L-citrulline, L-cysteine, L-glutamic acid, L-glutamine, glycine, L-histidine, L-isoleucine, L-leucine, L-lysine, L-methionine, L-ornithine, L-phenylalanine, L-proline, L-serine, L-threonine, L-tryptophan, L-tyrosine, and L-valine.

The phrase "aromatic L-amino acid" includes, for example, L-phenylalanine, L-tryptophan, and L-tyrosine. As L-histidine has an aromatic moiety such as an imidazole ring, the phrase "aromatic L-amino acid" can also include, besides the aforementioned aromatic L-amino acids, L-histidine.

The phrase "non-aromatic L-amino acid" includes, for example, L-alanine, L-arginine, L-asparagine, L-aspartic acid, L-citrulline, L-cysteine, L-glutamic acid, L-glutamine, glycine, L-isoleucine, L-leucine, L-lysine, L-methionine, L-ornithine, L-proline, L-serine, L-threonine, and L-valine. As the biosynthetic pathway of aromatic amino acids such as L-phenylalanine, L-tryptophan, or L-tyrosine is different from the biosynthetic pathway of L-histidine, the phrase "non-aromatic L-amino acid" can also include, besides the aforementioned non-aromatic L-amino acids, L-histidine.

An L-amino acid can belong to one or more L-amino acid families. As an example, the L-amino acid can belong to the glutamate family including L-arginine, L-glutamic acid, L-glutamine, and L-proline; the serine family including L-cysteine, glycine, and L-serine; the aspartate family including L-asparagine, L-aspartic acid, L-isoleucine, L-lysine, L-methionine, and L-threonine; the pyruvate family including L-alanine, L-isoleucine, L-valine, and L-leucine; and the aromatic family including L-phenylalanine, L-tryptophan, and L-tyrosine. As some L-amino acids can be the intermediate amino acids in a biosynthetic pathway of a particular L-amino acid, the aforementioned families of amino acids may also include other L-amino acids, for example, non-proteinogenic L-amino acids. For example, L-citrulline and L-ornithine are amino acids from the arginine biosynthetic pathway. Therefore, the glutamate family may include L-arginine, L-citrulline, L-glutamic acid, L-glutamine, L-ornithine, and L-proline L-Arginine, L-cysteine, L-glutamic acid, L-histidine, L-isoleucine, L-lysine, L-ornithine, L-phenylalanine, L-proline, L-threonine, L-tryptophan, and L-valine are particular examples. The pyruvate family amino acids such as L-alanine, L-isoleucine, L-valine, and L-leucine are preferable examples. The aromatic amino acids such as L-phenylalanine, L-tryptophan, and L-tyrosine are yet preferable examples. L-valine and L-phenylalanine are more preferable examples.

The phrase "L-amino acid" includes not only an L-amino acid in a free form, but may also include a salt or a hydrate of the L-amino acid, or an adduct formed by the L-amino acid and another organic or inorganic compound.

The bacteria belonging to the family Enterobacteriaceae can be from the genera *Enterobacter, Erwinia, Escherichia, Klebsiella, Morganella, Pantoea, Photorhabdus, Providencia, Salmonella, Yersinia*, and so forth, and can have the ability to produce an L-amino acid. Specifically, those classified into the family Enterobacteriaceae according to the taxonomy used in the NCBI (National Center for Biotechnology Information) database (ncbi.nlm.nih.gov/Taxonomy/Browser/wwwtax.cgi?id=543) can be used. Examples of strains from the family Enterobacteriaceae which can be modified include a bacterium of the genus *Escherichia, Enterobacter* or *Pantoea*.

Strains of *Escherichia* bacterium which can be modified to obtain *Escherichia* bacteria in accordance with the presently disclosed subject matter are not particularly limited, and specifically, those described in the work of Neidhardt et al. can be used (Bachmann, B. J., Derivations and genotypes of some mutant derivatives of *E. coli* K-12, p. 2460-2488. In F. C. Neidhardt et al. (ed.), *E. coli* and *Salmonella*: cellular and molecular biology, 2$^{nd}$ ed. ASM Press, Wash., D. C., 1996). The species *E. coli* is a particular example. Specific examples of *E. coli* include *E. coli* W3110 (ATCC 27325), *E. coli* MG1655 (ATCC 47076), and so forth, which are derived from the prototype wild-type strain, *E. coli* K-12 strain. These strains are available from, for example, the American Type Culture Collection (P.O. Box 1549, Manassas, Va. 20108, United States of America). That is, registration numbers are given to each of the strains, and the strains can be ordered by using these registration numbers (refer to atcc.org). The registration numbers of the strains are listed in the catalogue of the American Type Culture Collection.

Examples of the *Enterobacter* bacteria include *Enterobacter agglomerans, Enterobacter aerogenes*, and so forth. Examples of the *Pantoea* bacteria include *Pantoea ananatis*, and so forth. Some strains of *Enterobacter agglomerans* were recently reclassified into *Pantoea agglomerans, Pantoea ananatis* or *Pantoea stewartii* on the basis of nucleotide sequence analysis of 16S rRNA, etc. A bacterium belonging to any of the genus *Enterobacter* or *Pantoea* may be used so long as it is a bacterium classified into the family Enterobacteriaceae. When a *Pantoea ananatis* strain is bred by genetic engineering techniques, *Pantoea ananatis* AJ13355 strain (FERM BP-6614), AJ13356 strain (FERM BP-6615), AJ13601 strain (FERM BP-7207) and derivatives thereof can be used. These strains were identified as *Enterobacter agglomerans* when they were isolated, and deposited as *Enterobacter agglomerans*. However, they were recently re-classified as *Pantoea ananatis* on the basis of nucleotide sequencing of 16S rRNA and so forth as described above.

L-Amino Acid-Producing Bacteria

A bacterium belonging to the family Enterobacteriaceae and modified to overexpress the yajL gene, which is able to produce either an aromatic or a non-aromatic L-amino acid, can be used.

The bacterium may inherently have the L-amino acid-producing ability or may be modified to have an L-amino acid-producing ability by using a mutation method or DNA recombination techniques. The bacterium can be obtained by overexpressing the yajL gene in a bacterium which inherently has the ability to produce an L-amino acid. Alternatively, the bacterium can be obtained by imparting the ability to produce an L-amino acid to a bacterium already having the yajL gene overexpressed.

The bacterium can produced an L-amino acid either alone or as a mixture of two or more kinds of L-amino acids.

L-Arginine-Producing Bacteria

Examples of parental strains which can be used to derive L-arginine-producing bacteria include, but are not limited to, strains belonging to the genus *Escherichia* such as *E. coli* strain 237 (VKPM B-7925) (U.S. Patent Application 2002/058315 A1) and its derivative strains harboring mutant N-acetylglutamate synthase (RU2215783), *E. coli* strain 382 (VKPM B-7926) (EP1170358 A1), an arginine-producing strain into which argA gene encoding N-acetylglutamate synthetase is introduced therein (EP1170361 A1), and the like.

Examples of parental strains which can be used to derive L-arginine-producing bacteria also include strains in which expression of one or more genes encoding an L-arginine biosynthetic enzyme are enhanced. Examples of such genes include genes encoding N-acetyl-γ-glutamylphosphate reductase (argC), ornithine acetyltransferase (argJ), N-acetylglutamate kinase (argB), N-acetylornithine aminotransferase (argD), ornithine carbamoyltransferase (argF), argininosuccinate synthase (argG), argininosuccinate lyase (argH), and carbamoyl phosphate synthetase (carAB).

L-Citrulline-Producing Bacteria

Examples of parental strains which can be used to derive L-citrulline-producing bacteria include, but are not limited to, strains belonging to the genus *Escherichia* such as *E. coli* mutant N-acetylglutamate synthase strains 237/pMADS11, 237/pMADS12, and 237/pMADS13 (Russian patent No. 2215783, European patent No. 1170361 B1, U.S. Pat. No. 6,790,647 B2), *E. coli* strains 333 (VKPM B-8084) and 374 (VKPM B-8086), both harboring mutant feedback-resistant carbamoyl phosphate synthetase (Russian Patent RU2264459 C2), strains *E. coli*, in which α-ketoglutarate synthase activity is increased, and ferredoxin NADP$^+$ reductase, pyruvate synthase or α-ketoglutarate dehydrogenase activities are additionally modified (EP 2133417 A1), and strain *P. ananantis* NA1sucAsdhA, in which succinate dehydrogenase and α-ketoglutarate dehydrogenase activities are decreased (US Patent Application No 2009286290), and the like.

As L-citrulline is an intermediate of L-arginine biosynthetic pathway, examples of parent strains, which can be used to derive L-citrulline-producing bacteria, include strains in which expression of one or more genes encoding an L-arginine biosynthetic enzyme is enhanced. Examples of such genes include, but are not limited to, genes encoding N-acetylglutamate synthase (argA), N-acetylglutamate kinase (argB), N-acetylglutamyl phosphate reductase (argC), acetylornithine transaminase (argD), acetylornithine deacetylase (argE), ornithine carbamoyltransferase (argF/I), and carbamoyl phosphate synthetase (carAB), or combinations thereof.

L-citrulline-producing bacterium can be also easily obtained from any L-arginine-producing bacterium, for example *E. coli* 382 stain (VKPM B-7926), by inactivation of argininosuccinate synthase encoded by argG gene.

L-Cysteine-Producing Bacteria

Examples of parental strains which can be used to derive L-cysteine-producing bacteria include, but are not limited to, strains belonging to the genus *Escherichia* such as *E. coli* JM15 which is transformed with different cysE alleles encoding feedback-resistant serine acetyltransferases (U.S. Pat. No. 6,218,168, Russian patent No. 2279477), *E. coli* W3110 having overexpressed genes which encode proteins suitable for secreting substances toxic for cells (U.S. Pat. No. 5,972,663), *E. coli* strains having lowered cysteine desulfohydrase activity (JP11155571 A2), *E. coli* W3110 with increased activity of a positive transcriptional regulator for cysteine regulon encoded by the cysB gene (WO0127307 A1), and the like.

L-Glutamic Acid-Producing Bacteria

Examples of parental strains which can be used to derive L-glutamic acid-producing bacteria include, but are not limited to strains belonging to the genus *Escherichia* such as *E. coli* VL334thrC$^+$ (EP 1172433). The *E. coli* VL334 (VKPM B-1641) is an L-isoleucine and L-threonine auxotrophic strain having mutations in thrC and ilvA genes (U.S. Pat. No. 4,278,765). A wild-type allele of the thrC gene was transferred by the method of general transduction using a bacteriophage P1 grown on the wild-type *E. coli* strain K12 (VKPM B-7) cells. As a result, an L-isoleucine auxotrophic strain VL334thrC$^+$ (VKPM B-8961), which is able to produce L-glutamic acid, was obtained.

Examples of parental strains which can be used to derive the L-glutamic acid-producing bacteria include, but are not limited to strains in which expression of one or more genes encoding an L-glutamic acid biosynthetic enzyme are enhanced. Examples of such genes include genes encoding glutamate dehydrogenase (gdhA), glutamine synthetase (glnA), glutamate synthetase (gltAB), isocitrate dehydrogenase (icdA), aconitate hydratase (acnA, acnB), citrate synthase (gltA), phosphoenolpyruvate carboxylase (ppc), pyruvate carboxylase (pyc), pyruvate dehydrogenase (aceEF, lpdA), pyruvate kinase (pykA, pykF), phosphoenolpyruvate synthase (ppsA), enolase (eno), phosphoglyceromutase (pgmA, pgmI), phosphoglycerate kinase (pgk), glyceraldehyde-3-phophate dehydrogenase (gapA), triose phosphate isomerase (tpiA), fructose bisphosphate aldolase (fbp), phosphofructokinase (pfkA, pfkB), and glucose phosphate isomerase (pgi).

Examples of strains modified so that expression of the citrate synthetase gene, the phosphoenolpyruvate carboxylase gene, and/or the glutamate dehydrogenase gene is/are enhanced include those disclosed in EP1078989 A2, EP955368 A2, and EP952221 A2.

Examples of parental strains which can be used to derive the L-glutamic acid-producing bacteria also include strains having decreased or eliminated activity of an enzyme that catalyzes synthesis of a compound other than L-glutamic acid by branching off from an L-glutamic acid biosynthesis pathway. Examples of such enzymes include isocitrate lyase (aceA), α-ketoglutarate dehydrogenase (sucA), phosphotransacetylase (pta), acetate kinase (ack), acetohydroxy acid synthase (ilvG), acetolactate synthase (ilvI), formate acetyltransferase (pfl), lactate dehydrogenase (ldh), and glutamate decarboxylase (gadAB). Bacteria belonging to the genus *Escherichia* deficient in the α-ketoglutarate dehydrogenase activity or having a reduced α-ketoglutarate dehydrogenase activity and methods for obtaining them are described in U.S. Pat. Nos. 5,378,616 and 5,573,945. Specifically, these strains include the following:

E. coli W3110sucA::Km$^R$
E. coli AJ12624 (FERM BP-3853)
E. coli AJ12628 (FERM BP-3854)
E. coli AJ12949 (FERM BP-4881)

E. coli W3110sucA::Km$^R$ is a strain obtained by disrupting the α-ketoglutarate dehydrogenase gene (hereinafter referred to as "sucA gene") of E. coli W3110. This strain is completely deficient in α-ketoglutarate dehydrogenase.

Other examples of L-glutamic acid-producing bacterium include those which belong to the genus *Escherichia* and have resistance to an aspartic acid antimetabolite. These strains can also be deficient in the α-ketoglutarate dehydrogenase activity and include, for example, E. coli AJ13199 (FERM BP-5807) (U.S. Pat. No. 5,908,768), FFRM P-12379, which additionally has a low L-glutamic acid decomposing ability (U.S. Pat. No. 5,393,671), AJ13138 (FERM BP-5565) (U.S. Pat. No. 6,110,714), and the like.

Examples of L-glutamic acid-producing bacteria include mutant strains belonging to the genus *Pantoea* which are deficient in the α-ketoglutarate dehydrogenase activity or have a decreased α-ketoglutarate dehydrogenase activity, and can be obtained as described above. Such strains include *Pantoea ananatis* AJ13356. (U.S. Pat. No. 6,331,419). *Pantoea ananatis* AJ13356 was deposited at the National Institute of Bioscience and Human-Technology, Agency of Industrial Science and Technology, Ministry of International Trade and Industry (currently, Incorporated Administrative Agency, National Institute of Technology and Evaluation, International Patent Organism Depositary (NITE-IPOD), #120, 2-5-8 Kazusakamatari, Kisarazu-shi, Chiba-ken 292-0818, JAPAN) on Feb. 19, 1998 under an accession number of FERM P-16645. It was then converted to an international deposit under the provisions of Budapest Treaty on Jan. 11, 1999 and received an accession number of FERM BP-6615. *Pantoea ananatis* AJ13356 is deficient in α-ketoglutarate dehydrogenase activity as a result of disruption of the αKGDH-E1 subunit gene (sucA). The above strain was identified as *Enterobacter agglomerans* when it was isolated and deposited as the *Enterobacter agglomerans* AJ13356. However, it was recently re-classified as *Pantoea ananatis* on the basis of nucleotide sequencing of 16S rRNA and so forth. Although AJ13356 was deposited at the aforementioned depository as *Enterobacter agglomerans*, for the purposes of this specification, they are described as *Pantoea ananatis*.

L-Histidine-Producing Bacteria

Examples of parental strains which can be used to derive L-histidine-producing bacteria include, but are not limited to, strains belonging to the genus *Escherichia* such as E. coli strain 24 (VKPM B-5945, RU2003677), E. coli strain 80 (VKPM B-7270, RU2119536), E. coli NRRL B-12116-B12121 (U.S. Pat. No. 4,388,405), E. coli H-9342 (FERM BP-6675) and H-9343 (FERM BP-6676) (U.S. Pat. No. 6,344,347), E. coli H-9341 (FERM BP-6674) (EP1085087), E. coli AI80/pFM201 (U.S. Pat. No. 6,258,554), and the like.

Examples of parental strains which can be used to derive L-histidine-producing bacteria also include strains in which expression of one or more genes encoding an L-histidine biosynthetic enzyme are enhanced. Examples of such genes include genes encoding ATP phosphoribosyltransferase (hisG), phosphoribosyl-AMP cyclohydrolase (hisI), phosphoribosyl-AMP cyclohydrolase/phosphoribosyl-ATP pyrophosphatase (hisIE), phosphoribosylformimino-5-aminoimidazole carboxamide ribotide isomerase (hisA), amidotransferase (hisH), histidinol phosphate aminotransferase (hisC), histidinol phosphatase (hisB), histidinol dehydrogenase (hisD), and so forth.

It is known that the L-histidine biosynthetic enzymes encoded by hisG and hisBHAFI are inhibited by L-histidine, and therefore an L-histidine-producing ability can also be efficiently enhanced by introducing a mutation conferring resistance to the feedback inhibition into ATP phosphoribosyltransferase (Russian Patent Nos. 2003677 and 2119536).

Specific examples of strains having an L-histidine-producing ability include E. coli FERM-P 5038 and 5048 which have been transformed with a vector carrying a DNA encoding an L-histidine-biosynthetic enzyme (JP 56-005099 A), E. coli strains transformed with rht, a gene for an amino acid-export (EP1016710 A), E. coli 80 strain imparted with sulfaguanidine, DL-1,2,4-triazole-3-alanine, and streptomycin-resistance (VKPM B-7270, RU2119536), and so forth.

L-Isoleucine-Producing Bacteria

Examples of parental strains which can be used to derive L-isoleucine-producing bacteria include, but are not limited to, mutants having resistance to 6-dimethylaminopurine (JP 5-304969 A), mutants having resistance to an isoleucine analogue such as thiaisoleucine and isoleucine hydroxamate, and mutants additionally having resistance to DL-ethionine and/or arginine hydroxamate (JP 5-130882 A). In addition, recombinant strains transformed with genes encoding proteins involved in L-isoleucine biosynthesis, such as threonine deaminase and acetohydroxate synthase, can also be used as parental strains (JP 2-458 A, EP0356739 A1, and U.S. Pat. No. 5,998,178).

L-Leucine-Producing Bacteria

Examples of parental strains which can be used to derive L-leucine-producing bacteria include, but are not limited to, strains belonging to the genus *Escherichia* such as E. coli strains resistant to leucine (for example, the strain 57 (VKPM B-7386, U.S. Pat. No. 6,124,121)) or leucine analogs including β-2-thienylalanine, 3-hydroxyleucine, 4-azaleucine, 5,5,5-trifluoroleucine (JP 62-34397 B and JP 8-70879 A); E. coli strains obtained by the gene engineering method described in WO96/06926; E. coli H-9068 (JP 8-70879 A), and the like.

The bacterium can be improved by enhancing the expression of one or more genes involved in L-leucine biosynthesis. Examples include genes of the leuABCD operon, which can be represented by a mutant leuA gene encoding isopropylmalate synthase freed from feedback inhibition by L-leucine (U.S. Pat. No. 6,403,342). In addition, the bacterium can be improved by enhancing the expression of one or more genes encoding proteins which excrete L-amino acid from the bacterial cell. Examples of such genes include the b2682 and b2683 genes (ygaZH genes) (EP1239041 A2).

L-Lysine-Producing Bacteria

Examples of L-lysine-producing bacteria belonging to the family *Escherichia* include mutants having resistance to an L-lysine analogue. The L-lysine analogue inhibits growth of bacteria belonging to the genus *Escherichia*, but this inhibition is fully or partially desensitized when L-lysine is present in the medium. Examples of the L-lysine analogue include, but are not limited to, oxalysine, lysine hydroxamate, S-(2-aminoethyl)-L-cysteine (AEC), γ-methyllysine, α-chlorocaprolactam, and so forth. Mutants having resistance to these lysine analogues can be obtained by subjecting bacteria belonging to the genus *Escherichia* to a conventional artificial mutagenesis treatment. Specific examples of bacterial strains useful for producing L-lysine include *E. coli* AJ11442 (FERM BP-1543, NRRL B-12185; see U.S. Pat. No. 4,346,170) and *E. coli* VL611. In these microorganisms, feedback inhibition of aspartokinase by L-lysine is desensitized.

Examples of parental strains which can be used to derive L-lysine-producing bacteria also include strains in which expression of one or more genes encoding an L-lysine biosynthetic enzyme are enhanced. Examples of such genes include, but are not limited to, genes encoding dihydrodipicolinate synthase (dapA), aspartokinase (lysC), dihydrodipicolinate reductase (dapB), diaminopimelate decarboxylase (lysA), diaminopimelate dehydrogenase (ddh) (U.S. Pat. No. 6,040,160), phosphoenolpyrvate carboxylase (ppc), aspartate semialdehyde dehydrogenease (asd), and aspartase (aspA) (EP1253195 A1). In addition, the parental strains may have an increased level of expression of the gene involved in energy efficiency (cyo) (EP1170376 A1), the gene encoding nicotinamide nucleotide transhydrogenase (pntAB) (U.S. Pat. No. 5,830,716 A), the ybjE gene (WO2005/073390), or combinations thereof.

L-Amino acid-producing bacteria may have reduced or no activity of an enzyme that catalyzes a reaction which causes a branching off from the L-amino acid biosynthesis pathway and results in the production of another compound. Also, the bacteria may have reduced or no activity of an enzyme that negatively acts on L-amino acid synthesis or accumulation. Examples of such enzymes involved in L-lysine production include homoserine dehydrogenase, lysine decarboxylase (cadA, ldcC), malic enzyme, and so forth, and strains in which activities of these enzymes are decreased or deleted are disclosed in WO95/23864, WO96/17930, WO2005/010175, and so forth.

Expression of both the cadA and ldcC genes encoding lysine decarboxylase can be decreased in order to decrease or delete the lysine decarboxylase activity. Expression of the both genes can be decreased by, for example, the method described in WO2006/078039.

Examples of L-lysine-producing bacteria can include the *E. coli* WC196ΔcadAΔldcC/pCABD2 strain (WO2006/078039). The strain was constructed by introducing the plasmid pCABD2 containing lysine biosynthesis genes (U.S. Pat. No. 6,040,160) into the WC196 strain having disrupted cadA and ldcC genes which encode lysine decarboxylase.

The WC196 strain was bred from the W3110 strain, which was derived from *E. coli* K-12 by replacing the wild-type lysC gene on the chromosome of the W3110 strain with a mutant lysC gene encoding a mutant aspartokinase III in which threonine at position 352 was replaced with isoleucine, resulting in desensitization of the feedback inhibition by L-lysine (U.S. Pat. No. 5,661,012), and conferring AEC resistance to the resulting strain (U.S. Pat. No. 5,827,698). The WC196 strain was designated *E. coli* AJ13069, deposited at the National Institute of Bioscience and Human-Technology, Agency of Industrial Science and Technology (currently NITE-IPOD), #120, 2-5-8 Kazusakamatari, Kisarazu-shi, Chiba-ken 292-0818, JAPAN) on Dec. 6, 1994, and assigned an accession number of FERM P-14690. Then, it was converted to an international deposit under the provisions of the Budapest Treaty on Sep. 29, 1995, and assigned an accession number of FERM BP-5252 (U.S. Pat. No. 5,827,698).

The WC196ΔcadAΔldcC strain itself is also an exemplary L-lysine-producing bacterium. The WC196ΔcadAΔldcC was designated AJ110692 and deposited at the National Institute of Bioscience and Human-Technology, Agency of Industrial Science and Technology (currently (NITE-IPOD), #120, 2-5-8 Kazusakamatari, Kisarazu-shi, Chiba-ken 292-0818, JAPAN) on Oct. 7, 2008 as an international deposit under an accession number of FERM BP-11027.

L-Methionine-Producing Bacteria

Examples of L-methionine-producing bacteria and parent strains which can be used to derive L-methionine-producing bacteria include, but are not limited to, *Escherichia* bacteria strains such as strains AJ11539 (NRRL B-12399), AJ11540 (NRRL B-12400), AJ11541 (NRRL B-12401), AJ 11542 (NRRL B-12402) (patent GB2075055); strains 218 (VKPM B-8125) (patent RU2209248) and 73 (VKPM B-8126) (patent RU2215782) resistant to norleucine, the L-methionine analog, or the like. The strain *E. coli* 73 has been deposited in the Russian National Collection of Industrial Microorganisms (VKPM) FGUP GosNII Genetika (1 Dorozhny proezd, 1 Moscow 117545, Russian Federation) on May 14, 2001 under accession number VKPM B-8126, and was converted to an international deposit under the Budapest Treaty on Feb. 1, 2002. Furthermore, a methionine repressor-deficient strain and recombinant strains transformed with genes encoding proteins involved in L-methionine biosynthesis such as homoserine transsuccinylase and cystathionine γ-synthase (JP 2000-139471 A) can also be used as parent strains.

L-Ornithine-Producing Bacteria

L-ornithine-producing bacterium can be easily obtained from any L-arginine-producing bacterium, for example *E. coli* 382 stain (VKPM B-7926), by inactivation of ornithine carbamoyltransferase encoded by both argF and argI genes. Methods for inactivation of ornithine carbamoyltransferase are described herein.

L-Phenylalanine-Producing Bacteria

Examples of parental strains which can be used to derive L-phenylalanine-producing bacteria include, but are limited to strains belonging to the genus *Escherichia* such as *E. coli* AJ12739 (tyrA::Tn10, tyrR) (VKPM B-8197), *E. coli* HW1089 (ATCC 55371) harboring the mutant pheA34 gene (U.S. Pat. No. 5,354,672), *E. coli* MWEC101-b (KR8903681), *E. coli* NRRL B-12141, NRRL B-12145, NRRL B-12146 and NRRL B-12147 (U.S. Pat. No. 4,407, 952). Also, *E. coli* K-12 [W3110 (tyrA)/pPHAB (FERM BP-3566), *E. coli* K-12 [W3110 (tyrA)/pPHAD] (FERM BP-12659), *E. coli* K-12 [W3110 (tyrA)/pPHATerm] (FERM BP-12662), and *E. coli* K-12 [W3110 (tyrA)/pBR-aroG4, pACMAB] named as AJ 12604 (FERM BP-3579) may be used as a parental strain (EP488424 B1). Furthermore, L-phenylalanine-producing bacteria belonging to the genus *Escherichia* with an enhanced activity of the protein encoded by the yedA gene or the yddG gene may also be used (U.S. patent applications 2003/0148473 A1 and 2003/0157667 A1).

L-Proline-Producing Bacteria

Examples of parental strains which can be used to derive L-proline-producing bacteria include, but are not limited to, strains belonging to the genus *Escherichia* such as *E. coli* 702ilvA (VKPM B-8012) which is deficient in the ilvA gene and is able to produce L-proline (EP1172433 A1). The bacterium can be improved by enhancing the expression of one or more genes involved in L-proline biosynthesis. Examples of genes which can be used in L-proline-producing bacteria include the proB gene encoding glutamate kinase with desensitized feedback inhibition by L-proline (DE3127361 A1). In addition, the bacterium can be improved by enhancing the expression of one or more genes encoding proteins excreting L-amino acid from bacterial cell. Such genes are exemplified by b2682 and b2683 genes (ygaZH genes) (EP1239041 A2).

Examples of bacteria belonging to the genus *Escherichia*, which have an activity to produce L-proline include the following *E. coli* strains: NRRL B-12403 and NRRL B-12404 (GB Patent 2075056), VKPM B-8012 (Russian patent application No. 2000124295), plasmid mutants described in DE3127361 A1, plasmid mutants described by Bloom F. R. et al. in "The 15$^{th}$ Miami winter symposium", 1983, p. 34, and the like.

L-Threonine-Producing Bacteria

Examples of parental strains which can be used to derive L-threonine-producing bacteria include, but are not limited to, strains belonging to the genus *Escherichia* such as *E. coli* TDH-6/pVIC40 (VKPM B-3996) (U.S. Pat. No. 5,175,107, U.S. Pat. No. 5,705,371), *E. coli* 472T23/pYN7 (ATCC 98081) (U.S. Pat. No. 5,631,157), *E. coli* NRRL-21593 (U.S. Pat. No. 5,939,307), *E. coli* FERM BP-3756 (U.S. Pat. No. 5,474,918), *E. coli* FERM BP-3519 and FERM BP-3520 (U.S. Pat. No. 5,376,538), *E. coli* MG442 (Gusyatiner M. et al., Genetika (Russian), 1978, 14:947-956), *E. coli* VL643 and VL2055 (EP1149911 A2), and the like.

The strain TDH-6 is deficient in the thrC gene, as well as being sucrose-assimilative, and the ilvA gene has a leaky mutation. This strain also has a mutation in the rhtA gene, which imparts resistance to high concentrations of threonine or homoserine. The strain B-3996 contains the plasmid pVIC40 which was obtained by inserting a thrA*BC operon which includes a mutant thrA gene into a RSF1010-derived vector. This mutant thrA gene encodes aspartokinase homoserine dehydrogenase I which has substantially desensitized feedback inhibition by threonine. The strain B-3996 was deposited on Nov. 19, 1987 in the All-Union Scientific Center of Antibiotics (Russian Federation, 117105 Moscow, Nagatinskaya Street 3-A) under the accession number RIA 1867. The strain was also deposited in the Russian National Collection of Industrial Microorganisms (VKPM) FGUP GosNII Genetika (1 Dorozhny proezd, 1 Moscow 117545, Russian Federation) on Apr. 7, 1987 under the accession number VKPM B-3996.

*E. coli* VKPM B-5318 (EP0593792 A1) may also be used as a parental strain for deriving L-threonine-producing bacteria. The strain B-5318 is prototrophic with regard to isoleucine; and a temperature-sensitive lambda-phage C1 repressor and PR promoter replace the regulatory region of the threonine operon in plasmid pVIC40. The strain VKPM B-5318 was deposited in the Russian National Collection of Industrial Microorganisms (VKPM) FGUP GosNII Genetika (1 Dorozhny proezd, 1 Moscow 117545, Russian Federation) on May 3, 1990 under the accession number of VKPM B-5318.

The bacterium can be additionally modified to enhance expression of one or more of the following genes:
- the mutant thrA gene which encodes aspartokinase homoserine dehydrogenase I resistant to feedback inhibition by threonine;
- the thrB gene which encodes homoserine kinase;
- the thrC gene which encodes threonine synthase;
- the rhtA gene which encodes a putative transmembrane protein of the threonine and homoserine efflux system;
- the asd gene which encodes aspartate-β-semialdehyde dehydrogenase; and
- the aspC gene which encodes aspartate aminotransferase (aspartate transaminase);

The thrA gene which encodes aspartokinase I and homoserine dehydrogenase I of *E. coli* has been elucidated (KEGG, Kyoto Encyclopedia of Genes and Genomes, entry No. b0002; GenBank accession No. NC_000913.2; nucleotide positions: 337 to 2,799; Gene ID: 945803). The thrA gene is located between the thrL and thrB genes on the chromosome of *E. coli* K-12.

The thrB gene which encodes homoserine kinase of *E. coli* has been elucidated (KEGG entry No. b0003; GenBank accession No. NC_000913.2; nucleotide positions: 2,801 to 3,733; Gene ID: 947498). The thrB gene is located between the thrA and thrC genes on the chromosome of *E. coli* K-12.

The thrC gene which encodes threonine synthase of *E. coli* has been elucidated (KEGG entry No. b0004; GenBank accession No. NC_000913.2; nucleotide positions: 3,734 to 5,020; Gene ID: 945198). The thrC gene is located between the thrB and yaaX genes on the chromosome of *E. coli* K-12. All three genes function as a single threonine operon thrABC. To enhance expression of the threonine operon, the attenuator region which affects the transcription is desirably removed from the operon (WO2005049808 A1, WO2003097839 A1).

The mutant thrA gene which encodes aspartokinase I and homoserine dehydrogenase I resistant to feedback inhibition by L-threonine, as well as, the thrB and thrC genes can be obtained as one operon from the well-known plasmid pVIC40 which is present in the L-threonine-producing *E. coli* strain VKPM B-3996. Plasmid pVIC40 is described in detail in U.S. Pat. No. 5,705,371.

The rhtA gene which encodes a protein of the threonine and homoserine efflux system (an inner membrane transporter) of *E. coli* has been elucidated (KEGG entry No. b0813; GenBank accession No. NC_000913.2; nucleotide positions: 848,433 to 849,320, complement; Gene ID: 947045). The rhtA gene is located between the dps and ompX genes on the chromosome of *E. coli* K-12 close to the glnHPQ operon, which encodes components of the glutamine transport system. The rhtA gene is identical to the ybiF gene (KEGG entry No. B0813).

The asd gene which encodes aspartate-β-semialdehyde dehydrogenase of *E. coli* has been elucidated (KEGG entry No. b3433; GenBank accession No. NC_000913.2; nucleotide positions: 3,571,798 to 3,572,901, complement; Gene ID: 947939). The asd gene is located between the glgB and gntU gene on the same strand (yhgN gene on the opposite strand) on the chromosome of *E. coli* K-12.

Also, the aspC gene which encodes aspartate aminotransferase of *E. coli* has been elucidated (KEGG entry No. b0928; GenBank accession No. NC_000913.2; nucleotide positions: 983,742 to 984,932, complement; Gene ID: 945553). The aspC gene is located between the ycbL gene on the opposite strand and the ompF gene on the same strand on the chromosome of *E. coli* K-12.

L-Tryptophan-Producing Bacteria

Examples of parental strains which can be used to derive the L-tryptophan-producing bacteria include, but are not limited to, strains belonging to the genus *Escherichia* such as *E. coli* JP4735/pMU3028 (DSM10122) and JP6015/pMU91 (DSM10123) deficient in the tryptophanyl-tRNA synthetase encoded by mutant trpS gene (U.S. Pat. No. 5,756,345), *E. coli* SV164 (pGH5) having a serA allele encoding phosphoglycerate dehydrogenase free from feedback inhibition by serine and a trpE allele encoding anthranilate synthase free from feedback inhibition by tryptophan (U.S. Pat. No. 6,180,373), *E. coli* AGX17 (pGX44) (NRRL B-12263) and AGX6(pGX50)aroP (NRRL B-12264) deficient in the enzyme tryptophanase (U.S. Pat. No. 4,371,614), *E. coli* AGX17/pGX50,pACKG4-pps in which a phosphoenolpyruvate-producing ability is enhanced (WO9708333, U.S. Pat. No. 6,319,696), and the like may be used. L-tryptophan-producing bacteria belonging to the genus *Escherichia* with an enhanced activity of the identified protein encoded by and the yedA gene or the yddG gene may also be used (U.S. patent applications 2003/0148473 A1 and 2003/0157667 A1).

Examples of parental strains which can be used to derive the L-tryptophan-producing bacteria also include strains in which one or more activities of the enzymes selected from anthranilate synthase, phosphoglycerate dehydrogenase, and tryptophan synthase are enhanced. The anthranilate synthase and phosphoglycerate dehydrogenase are both subject to feedback inhibition by L-tryptophan and L-serine, so that a mutation desensitizing the feedback inhibition may be introduced into these enzymes. Specific examples of strains having such a mutation include an *E. coli* SV164 which harbors desensitized anthranilate synthase and a transformant strain obtained by introducing into the *E. coli* SV164 the plasmid pGH5 (WO 94/08031), which contains a mutant serA gene encoding feedback-desensitized phosphoglycerate dehydrogenase.

Examples of parental strains which can be used to derive the L-tryptophan-producing bacteria also include strains into which the tryptophan operon which contains a gene encoding desensitized anthranilate synthase has been introduced (JP 57-71397 A, JP 62-244382 A, U.S. Pat. No. 4,371,614). Moreover, L-tryptophan-producing ability may be imparted by enhancing expression of a gene which encodes tryptophan synthase, among tryptophan operons (trpBA). The tryptophan synthase consists of α and β subunits which are encoded by the trpA and trpB genes, respectively. In addition, L-tryptophan-producing ability may be improved by enhancing expression of the isocitrate lyase-malate synthase operon (WO2005/103275).

L-Valine-Producing Bacteria

Examples of parental strains which can be used to derive L-valine-producing bacteria include, but are not limited to, strains which have been modified to overexpress the ilvGMEDA operon (U.S. Pat. No. 5,998,178). It is desirable to remove the region of the ilvGMEDA operon which is required for attenuation so that expression of the operon is not attenuated by the L-valine that is produced. Furthermore, the ilvA gene in the operon is desirably disrupted so that threonine deaminase activity is decreased.

Examples of parental strains for deriving L-valine-producing bacteria also include mutants having a mutation of aminoacyl-tRNA synthetase (U.S. Pat. No. 5,658,766). For example, *E. coli* VL1970, which has a mutation in the ileS gene encoding isoleucine tRNA synthetase, can be used. *E. coli* VL1970 was deposited in the Russian National Collection of Industrial Microorganisms (VKPM) FGUP GosNII Genetika (1 Dorozhny proezd, 1 Moscow 117545, Russian Federation) on Jun. 24, 1988 under the accession number VKPM B-4411.

Furthermore, mutants requiring lipoic acid for growth and/or lacking $H^+$-ATPase can also be used as parental strains (WO96/06926).

Parent strains for deriving L-valine-producing bacteria also include *E. coli* H81 strain (VKPM B-8066; see, for example, EP1942183 B1), NRRL B-12287 and NRRL B-12288 (U.S. Pat. No. 4,391,907), VKPM B-4411 (U.S. Pat. No. 5,658,766), VKPM B-7707 (European patent application EP1016710 A2) or the like.

The bacterium of the present invention belonging to the family Enterobacteriaceae has been modified to overexpress the yajL gene.

The phrase "a bacterium modified to overexpress the yajL gene" can mean that the bacterium has been modified in such a way that in the modified bacterium the total enzymatic activity of the corresponding gene protein product such as YajL is increased as compared with, or the expression level of the yajL gene is higher than that level in, a non-modified strain, for example, a wild-type or parental strain as described above and hereinafter. Examples of a non-modified strain serving as a reference for the above comparison can include a wild-type strain of a microorganism belonging to the genus *Escherichia* such as the *E. coli* MG1655 strain (ATCC 47076), W3110 strain (ATCC 27325), and so forth.

The phrase "the yajL gene is overexpressed" can mean that the total enzymatic activity of the corresponding gene protein product such as the YajL protein is increased by, for example, introducing and/or increasing the copy number of the yajL gene in bacterial genome, or increasing the activity per molecule (may be referred to as a specific activity) of the protein encoded by said gene, as compared with a non-modified strain. The bacterium can be modified so that the activity of the YajL protein per cell is increased to 150% or more, 200% or more, 300% or more, of the activity of a non-modified strain. The chaperone activity of YajL can be used to determine a specific enzymatic activity of the protein per mg. For example, citrate synthase can be used as a control protein to measure refolding activity of YajL under reducing or oxidizing conditions (Kthiri F. et al., *J. Biol. Chem.*, 2010, 285:10328-10336). The protein concentration can be determined by the Bradford protein assay (Bradford M. M., *Anal. Biochem.*, 1976, 72:248-254) using bovine serum albumin as a standard.

The phrase "the yajL gene is overexpressed" can also mean that the expression level of the yajL gene is higher than that level in a non-modified strain. Therefore, the phrase "the yajL gene is overexpressed" is equivalent to the phrase "expression of the yajL gene is enhanced".

Methods which can be used to enhance expression of the yajL gene include, but are not limited to, increasing the yajL gene copy number in bacterial genome (in the chromosome and/or in the autonomously replicable plasmid) and/or introducing the yajL gene into a vector that is able to increase the copy number and/or the expression level of the yajL gene in a bacterium of the family Enterobacteriaceae according to genetic engineering methods known to the one skilled in the art.

Examples of the vectors include, but are not limited to, broad-host-range plasmids such as pMW118/119, pBR322, pUC19, and the like. Multiple copies of the yajL gene can also be introduced into the chromosomal DNA of a bacterium by, for example, homologous recombination, Mu-driven integration, or the like. Homologous recombination can be carried out using sequence with multiple copies in the chromosomal DNA. Sequences with multiple copies in the chromosomal DNA include, but are not limited to, repetitive DNA or inverted repeats present at the end of a transposable element. In addition, it is possible to incorporate the yajL gene into a transposon and allow it to be transferred to introduce multiple copies of the yajL gene into the chromosomal DNA. By using Mu-driven integration, more than 3 copies of the gene can be introduced into the chromosomal DNA during a single act (Akhverdyan V. Z. et al., *Biotechnol.* (Russian), 2007, 3:3-20).

Enhancing of the yajL gene expression can also be achieved by increasing the expression level of the yajL gene by modification of adjacent regulatory regions of the yajL gene or introducing native and/or modified foreign regulatory regions. Regulatory regions or sequences can be exemplified by promoters, enhancers, attenuators and termination signals, anti-termination signals, ribosome-binding sites (RBS) and other expression control elements (e.g., regions to which repressors or inducers bind and/or binding sites for transcriptional and translational regulatory proteins, for example, in the transcribed mRNA). Such regulatory regions are described, for example, in Sambrook J., Fritsch E. F. and Maniatis T., "Molecular Cloning: A Laboratory Manual", $2^{nd}$ ed., Cold Spring Harbor Laboratory Press (1989). Modifications of regions controlling gene(s) expression can be combined with increasing the copy number of the modified gene(s) in bacterial genome using the known methods (see, for example, Akhverdyan V. Z. et al., *Appl. Microbiol. Biotechnol.*, 2011, 91:857-871; Tyo K. E. J. et al., *Nature Biotechnol.*, 2009, 27:760-765).

The exemplary promoters enhancing the yajL gene expression can be the potent promoters that are stronger than the native yajL promoter. For example, the lac promoter, the trp promoter, the trc promoter, the tac promoter, the $P_R$ or the $P_L$ promoters of lambda phage are all known to be potent promoters. Potent promoters providing a high level of gene expression in a bacterium belonging to the family Enterobacteriaceae can be used. Alternatively, the effect of a promoter can be enhanced by, for example, introducing a mutation into the promoter region of the yajL gene to obtain a stronger promoter function, thus resulting in the increased transcription level of the yajL gene located downstream of the promoter. Furthermore, it is known that substitution of several nucleotides in the Shine-Dalgarno (SD) sequence, and/or in the spacer between the SD sequence and the start codon, and/or a sequence immediately upstream and/or downstream from the start codon in the ribosome-binding site greatly affects the translation efficiency of mRNA. For example, a 20-fold range in the expression levels was found, depending on the nature of the three nucleotides preceding the start codon (Gold L. et al., *Annu. Rev. Microbiol.*, 1981, 35:365-403; Hui A. et al., *EMBO J.*, 1984, 3:623-629).

The copy number, presence or absence of the gene can be measured, for example, by restricting the chromosomal DNA followed by Southern blotting using a probe based on the gene sequence, fluorescence in situ hybridization (FISH), and the like. The level of gene expression can be determined by measuring the amount of mRNA transcribed from the gene using various well-known methods, including Northern blotting, quantitative RT-PCR, and the like. The amount of the protein encoded by the gene can be measured by known methods including SDS-PAGE followed by immunoblotting assay (Western blotting analysis), or mass spectrometry analysis of the protein samples, and the like.

Methods for manipulation with recombinant molecules of DNA and molecular cloning such as preparation of plasmid DNA, digestion, ligation and transformation of DNA, selection of an oligonucleotide as a primer, incorporation of mutations, and the like may be ordinary methods well-known to the person skilled in the art. These methods are described, for example, in Sambrook J., Fritsch E. F. and Maniatis T., "Molecular Cloning: A Laboratory Manual", $2^{nd}$ ed., Cold Spring Harbor Laboratory Press (1989) or Green M. R. and Sambrook J. R., "Molecular Cloning: A Laboratory Manual", $4^{th}$ ed., Cold Spring Harbor Laboratory Press (2012); Bernard R. Glick, Jack J. Pasternak and Cheryl L. Patten, "Molecular Biotechnology: principles and applications of recombinant DNA", $4^{th}$ ed., Washington, D.C., ASM Press (2009).

The yajL gene encodes the oxidative-stress-resistance chaperone YajL (KEGG, Kyoto Encyclopedia of Genes and Genomes, entry No. b0424; Protein Knowledgebase, Uni- ProtKB/Swiss-Prot, accession No. Q46948). The yajL gene (GenBank accession No. NC_000913.2; nucleotide positions: 442275 to 442865, complement; Gene ID: 945066) is located between the panE gene on the same strand and the thiI gene on the opposite strand on the chromosome of *E. coli* strain K-12. The nucleotide sequence of the yajL gene and the amino acid sequence of the YajL protein encoded by the yajL gene are shown in SEQ ID NO: 1 and SEQ ID NO: 2, respectively. In some microorganisms, the YajL protein has been mistakenly described as ThiJ involved in thiamine metabolism (EcoGene: EG13272; ecogene.org/old/geneinfo.php?eg_id=EG13272). This phenotype is now attributed to the adjacent thiI gene (T. Begley, personal communication cited in Mueller E. G. et al., Identification of a gene involved in the generation of 4-thio-uridine in tRNA, *Nucleic Acids Res.*, 1998, 26(11):2606-2610).

Since there may be some differences in DNA sequences between the genera, species or strains of the family Enterobacteriaceae, the yajL gene is not limited to the gene shown in SEQ ID NO: 1, but may include genes which are variant nucleotide sequences of or homologous to SEQ ID NO: 1, and which encode variants of the YajL protein.

The phrase "a variant protein" can mean a protein which has one or several changes in the sequence compared with SEQ ID NO: 2, whether they are substitutions, deletions, insertions, and/or additions of one or several amino acid residues, but still maintains an activity or function similar to that of the YajL protein, or the three-dimensional structure of the YajL protein is not significantly changed relative to the wild-type or non-modified protein. The number of changes in the variant protein depends on the position in the three-dimensional structure of the protein or the type of amino acid residues. It can be, but is not strictly limited to, 1 to 30, in another example 1 to 15, in another example 1 to 10, and in another example 1 to 5, in SEQ ID NO: 2. This is because some amino acids have high homology to one another so that the activity or function is not affected by such a change, or the three-dimensional structure of YajL is not significantly changed relative to the wild-type or non-modified protein. Therefore, the protein variants encoded by the yajL gene may have a homology, defined as the parameter "identity" when using the computer program BLAST, of not less than 70%, not less than 80%, not less than 90%, not less than 95%, not less than 98%, or not less than 99% with respect to the entire amino acid sequence shown in SEQ ID NO: 2, as long as the activity or function of the YajL protein is maintained, or the three-dimensional structure of YajL is not significantly changed relative to the wild-type or non-modified protein.

The exemplary substitution, deletion, insertion, and/or addition of one or several amino acid residues can be a conservative mutation(s). The representative conservative mutation is a conservative substitution. The conservative substitution can be, but is not limited to, a substitution, wherein substitution takes place mutually among Phe, Trp and Tyr, if the substitution site is an aromatic amino acid; among Ala, Leu, Ile and Val, if the substitution site is a hydrophobic amino acid; between Glu, Asp, Gln, Asn, Ser, His and Thr, if the substitution site is a hydrophilic amino acid; between Gln and Asn, if the substitution site is a polar amino acid; among Lys, Arg and His, if the substitution site is a basic amino acid; between Asp and Glu, if the substitution site is an acidic amino acid; and between Ser and Thr, if the substitution site is an amino acid having hydroxyl group. Examples of conservative substitutions include substitution of Ser or Thr for Ala, substitution of Gln, His or Lys for Arg, substitution of Glu, Gln, Lys, His or Asp for Asn, substitution Asn, Glu or Gln for Asp, substitution of Ser or Ala for Cys, substitution Asn, Glu, Lys, His, Asp or Arg for Gln, substitution Asn, Gln, Lys or Asp for Glu, substitution of Pro for Gly, substitution Asn, Lys, Gln, Arg or Tyr for His, substitution of Leu, Met, Val or Phe for Ile, substitution of Ile, Met, Val or Phe for Leu, substitution Asn, Glu, Gln, His or Arg for Lys, substitution of Ile, Leu, Val or Phe for Met, substitution of Trp, Tyr, Met, Ile or Leu for Phe, substitution of Thr or Ala for Ser, substitution of Ser or Ala for Thr, substitution of Phe or Tyr for Trp, substitution of His, Phe or Trp for Tyr, and substitution of Met, Ile or Leu for Val.

The exemplary substitution, deletion, insertion, and/or addition of one or several amino acid residues can also be a non-conservative mutation(s) provided that the mutation(s) is/are compensated by one or more secondary mutation(s) in the different position(s) of amino acids sequence so that the activity or function of the variant protein is maintained and similar to that of the YajL protein, or the three-dimensional structure of YajL is not significantly changed relative to the wild-type or non-modified protein.

To evaluate the degree of protein or DNA homology, several calculation methods can be used, such as BLAST search, FASTA search and ClustalW method. The BLAST (Basic Local Alignment Search Tool, ncbi.nlm.nih.gov/BLAST/) search is the heuristic search algorithm employed by the programs blastp, blastn, blastx, megablast, tblastn, and tblastx; these programs ascribe significance to their findings using the statistical methods of Samuel K. and Altschul S. F. ("Methods for assessing the statistical significance of molecular sequence features by using general scoring schemes" *Proc. Natl. Acad. Sci. USA*, 1990, 87:2264-2268; "Applications and statistics for multiple high-scoring segments in molecular sequences". *Proc. Natl. Acad. Sci. USA*, 1993, 90:5873-5877). The computer program BLAST calculates three parameters: score, identity and similarity. The FASTA search method is described by Pearson W. R. ("Rapid and sensitive sequence comparison with FASTP and FASTA", *Methods Enzymol.*, 1990, 183: 63-98). The ClustalW method is described by Thompson J. D. et al. ("CLUSTAL W: improving the sensitivity of progressive multiple sequence alignment through sequence weighting, position-specific gap penalties and weight matrix choice", *Nucleic Acids Res.*, 1994, 22:4673-4680).

Moreover, the yajL gene can be a variant nucleotide sequence. The phrase "a variant nucleotide sequence" can mean a nucleotide sequence which encodes "a variant protein" using any synonymous amino acid codons according to the standard genetic code table (see, e.g., Lewin B., "Genes VIII", 2004, Pearson Education, Inc., Upper Saddle River, N.J. 07458). Therefore, the yajL gene can be a variant nucleotide sequence due to degeneracy of genetic code.

The phrase "a variant nucleotide sequence" can also mean, but is not limited to, a nucleotide sequence which hybridizes under stringent conditions with the nucleotide sequence complementary to the sequence shown in SEQ ID NO: 1, or a probe which can be prepared from the nucleotide sequence under stringent conditions provided that it encodes active or functional protein. "Stringent conditions" include those under which a specific hybrid, for example, a hybrid having homology, defined as the parameter "identity" when using the computer program BLAST, of not less than 60%, not less than 70%, not less than 80%, not less than 90%, not less than 95%, not less than 96%, not less than 97%, not less than 98%, or not less than 99% is formed, and a non-specific hybrid, for example, a hybrid having homology lower than the above is not formed. For example, stringent conditions can be exemplified by washing one time or more, or in another example, two or three times, at a salt concentration of 1×SSC (standard sodium citrate or standard sodium chloride), 0.1% SDS (sodium dodecyl sulphate), or in another example, 0.1×SSC, 0.1% SDS at 60° C. or 65° C. Duration of washing depends on the type of membrane used for blotting and, as a rule, should be what is recommended by the manufacturer. For example, the recommended duration of washing for the Amersham Hybond™-N+ positively charged nylon membrane (GE Healthcare) under stringent conditions is 15 minutes. The washing step can be performed 2 to 3 times. As the probe, a part of the sequence complementary to the sequences shown in SEQ ID NO: 1 may also be used. Such a probe can be produced by PCR using oligonucleotides as primers prepared on the basis of the sequence shown in SEQ ID NO: 1 and a DNA fragment containing the nucleotide sequence as a template. The length of the probe is recommended to be >50 bp; it can be suitably selected depending on the hybridization conditions, and is usually 100 bp to 1 kbp. For example, when a DNA fragment having a length of about 300 bp is used as the probe, the washing conditions after hybridization can be exemplified by 2×SSC, 0.1% SDS at 50° C., 60° C. or 65° C.

As the gene encoding the YajL protein of the species *E. coli* has already been elucidated (see above), the yajL gene encoding the YajL protein, and the variant nucleotide sequences encoding variant proteins of YajL protein can be obtained by PCR (polymerase chain reaction; refer to White T. J. et al., The polymerase chain reaction, *Trends Genet.*, 1989, 5:185-189) from a bacterium belonging to the family Enterobacteriaceae utilizing primers prepared based on the nucleotide sequence of the yajL gene; or the site-directed mutagenesis method by treating a DNA containing the wild-type yajL gene in vitro, for example, with hydroxylamine, or a method for treating a microorganism, for example, a bacterium belonging to the family Enterobacteriaceae harboring the wild-type yajL gene with ultraviolet (UV) irradiation or a mutating agent such as N-methyl-N'-nitro-N-nitrosoguanidine (NTG) and nitrous acid usually used for the such treatment; or chemically synthesized as full-length gene structure. Genes encoding the YajL protein or its variant proteins of other microorganisms of the family Enterobacteriaceae can be obtained in a similar manner.

The phrase "a wild-type protein" can mean a native protein naturally produced by a wild-type or parent bacterial strain of the family Enterobacteriaceae, for example, by the wild-type *E. coli* MG1655 strain. A wild-type protein can be encoded by the "wild-type gene", or the "non-modified gene" naturally occurring in genome of a wild-type bacterium.

The bacterium as described herein can be obtained by modifying a bacterium inherently having an ability to produce an L-amino acid to overexpress the yajL gene, for example, by introducing the aforementioned DNAs into the bacterium. Alternatively, the bacterium as described herein can be obtained by imparting the ability to produce an L-amino acid to a bacterium already modified to overexpress the yajL gene.

The bacterium can have, in addition to the properties already mentioned, other specific properties such as various nutrient requirements, drug resistance, drug sensitivity, and drug dependence, without departing from the scope of the present invention.

2. Method

A method of the present invention includes the method for producing an L-amino acid such as L-alanine, L-arginine, L-asparagine, L-aspartic acid, L-citrulline, L-cysteine, L-glutamic acid, L-glutamine, glycine, L-histidine, L-isoleucine, L-leucine, L-lysine, L-methionine, L-ornithine, L-phenylalanine, L-proline, L-serine, L-threonine, L-tryptophan, L-tyrosine, and L-valine, or a mixture thereof. The method for producing an L-amino acid can include the steps of cultivating the bacterium in a culture medium to allow the L-amino acid to be produced, excreted, and/or accumulated in the culture medium or in the bacterial cells, and collecting the L-amino acid from the culture medium and/or the bacterial cells. The L-amino acid can be produced in a salt or a hydrate form thereof, or a combination thereof. For example, sodium, potassium, ammonium, and the like salts of the L-amino acid can be produced by the method. The L-amino acid can be produced in an adduct form thereof with, for example, another organic or inorganic compound. Specifically, a monochlorhydrate salt of an L-amino acid can be produced by the method such as monochlorhydrate salt of L-lysine.

The cultivation of the bacterium, and collection and purification of L-amino acid from the medium and the like may be performed in a manner similar to conventional fermentation methods wherein L-amino acid is produced using a microorganism. The culture medium for production of the L-amino acid can be either a synthetic or natural medium such as a typical medium that contains a carbon source, a nitrogen source, a sulphur source, inorganic ions, and other organic and inorganic components as required. As the carbon source, saccharides such as glucose, sucrose, lactose, galactose, fructose, arabinose, maltose, xylose, trehalose, ribose, and hydrolyzates of starches; alcohols such as ethanol, glycerol, mannitol, and sorbitol; organic acids such as gluconic acid, fumaric acid, citric acid, malic acid, and succinic acid; fatty acid, and the like can be used. As the nitrogen source, inorganic ammonium salts such as ammonium sulfate, ammonium chloride, and ammonium phosphate; organic nitrogen such as of soy bean hydrolyzates; ammonia gas; aqueous ammonia; and the like can be used. The sulphur source can include ammonium sulphate, magnesium sulphate, ferrous sulphate, manganese sulphate, and the like. Vitamins such as vitamin B1, required substances, for example, organic nutrients such as nucleic acids such as adenine and RNA, or yeast extract, and the like may be present in appropriate, even if trace, amounts. Other than these, small amounts of calcium phosphate, iron ions, manganese ions, and the like may be added, if necessary.

Cultivation can be performed under aerobic conditions for 16 to 72 h, or for 32 to 68 h; the culture temperature during cultivation can be controlled within 30 to 45° C., or within 30 to 37° C.; and the pH can be adjusted between 5 and 8, or between 6 and 7.5. The pH can be adjusted by using an inorganic or organic acidic or alkaline substance, as well as ammonia gas.

After cultivation, solids such as cells and cell debris can be removed from the liquid medium by centrifugation or membrane filtration, and then the target L-amino acid can be recovered from the fermentation liquor by any combination of conventional techniques such as concentration, ion-exchange chromatography, and crystallization.

EXAMPLES

The present invention will be more precisely explained below with reference to the following non-limiting Examples.

Example 1

Construction of the *E. coli* L-Valine-Producing Strain Modified to Overexpress the yajL Gene 1.1 Construction of the *E. coli* MG1655 Strain Having Modified a Regulatory Region of yajL Expression of the yajL gene in *E. coli* was changed using the method developed by Datsenko K. A. and Wanner B. L. called "λRed/ET-mediated integration" (Datsenko K. A. and Wanner B. L., *Proc. Natl. Acad. Sci. USA*, 2000, 97(12): 6640-6645). According to this procedure, the PCR primers P1 (SEQ ID NO: 3) and P2 (SEQ ID NO: 4), which are homologous to both regions adjacent to the yajL gene and the gene conferring chloramphenicol resistance ($Cm^R$) and the regions adjacent to the promoter in the template chromosome, were constructed. The chromosome of the chloramphenicol-resistant *E. coli* strain MG1655 which contains a tac-like promoter having the structure of the −35 region as TGGCAA (from 5'-end to 3'-end) upstream lacZ (refer to Table 1, clone 7 in Katashkina J. L. et al., Tuning the expression level of a gene located on a bacterial chromosome, *Mol. Biol.* (Mosk., in Russian), 2005, 39(5):719-726) was used as the template in PCR reaction. Conditions for PCR were as follows: denaturation for 3 min at 95° C.; profile for 35 cycles: 1 min at 95° C., 1 min at 58° C., 1 min at 72° C.; final elongation for 5 min at 72° C. The obtained DNA-fragment 1 (1,768 bp) (SEQ ID NO: 5) was purified in an agarose gel and used for electroporation of the strain *E. coli* MG1655 (ATCC 47076) containing the plasmid pKD46 with a temperature-sensitive replication origin. The plasmid pKD46 (Datsenko K. A. and Wanner B. L., *Proc. Natl. Acad. Sci. USA*, 2000, 97(12):6640-6645) includes a 2,154 nt (31088-33241) DNA-fragment of phage λ (GenBank accession No. J02459) and contains genes of the λRed homologous recombination system (γ, β, exo genes) under the control of arabinose-inducible $P_{araB}$ promoter. The plasmid pKD46 is necessary to integrate the DNA-fragment into the chromosome of strain *E. coli* MG1655.

Electrocompetent cells were prepared as follows: *E. coli* MG1655 cells were grown overnight at 30° C. in LB-medium (Sambrook, J. and Russell, D. W. "Molecular Cloning: A Laboratory Manual", 3$^{rd}$ ed., Cold Spring Harbor Laboratory Press (2001)) containing ampicillin (100 mg/L), and the culture was diluted 100 times with 5 mL of SOB-medium (Sambrook J., Fritsch E. F. and Maniatis T., "Molecular Cloning: A Laboratory Manual", 2$^{nd}$ ed., Cold Spring Harbor Laboratory Press (1989)) containing ampicillin (100 mg/L) and L-arabinose (1 mM). The obtained culture was grown with aeration (250 rpm) at 30° C. to an $OD_{600}$ of ~0.6 and then made electrocompetent by concentrating 100-fold and washing three times with ice-cold deionized $H_2O$. Electroporation was performed using 70 μL of cells and ~100 ng of the DNA-fragment 1. Then, cells were incubated with 1 mL of SOC-medium (Sambrook J., Fritsch E. F. and Maniatis T., "Molecular Cloning: A Laboratory Manual", 2$^{nd}$ ed., Cold Spring Harbor Laboratory Press (1989)) at 37° C. for 2.5 h, placed onto the plates containing LB-medium (Sambrook, J. and Russell, D. W. "Molecular Cloning: A Laboratory Manual", 3$^{rd}$ ed., Cold Spring Harbor Laboratory Press (2001)), agar (1.5%) and chloramphenicol (20 mg/L), and grown at 37° C. to select $Cm^R$-recombinants. To eliminate the pKD46 plasmid, 1 passage on L-agar with chloramphenicol (20 mg/L) at 42° C. were performed, and the obtained colonies were tested for sensitivity to ampicillin. Thus the strain *E. coli* MG1655 $P_{tac7}$-yajL was obtained.

1.2 Verification of a Modification of the Regulatory Region of yajL

Mutants containing the replacement of a promoter region of the yajL gene marked with Cm$^R$-gene (cat) were verified by PCR using locus-specific primers P3 (SEQ ID NO: 6) and P4 (SEQ ID NO: 7). Conditions for PCR were as follows: denaturation for 3 min at 94° C.; profile for 30 cycles: 30 sec at 94° C., 30 sec at 58° C., 2 min at 72° C.; final elongation for 6 min at 72° C. DNA-fragment 2, obtained in the reaction with the chromosomal DNA from the parent strain *E. coli* MG1655 as the template, was 966 bp in length (SEQ ID NO: 8). DNA-fragment 3, obtained in the reaction with the chromosomal DNA from the mutant strain *E. coli* MG1655 P$_{tac7}$-yajL as a template, was 1,820 bp in length (SEQ ID NO: 9).

1.3. Construction of the *E. coli* L-Valine-Producing Strain

The yajL gene under control of P$_{tac7}$ promoter was introduced into valine-producing *E. coli* strain H81 (Russian patent No. 2355763, EP1942183 B1) by P1-transduction (Miller J. H. "Experiments in molecular genetics", Cold Spring Harbor Laboratory, Cold Spring Harbor (1972)). The *E. coli* MG1655 P$_{tac7}$-yajL strain (see Example 1.1) was used as a donor. The strain H81 was deposited in the Russian National Collection of Industrial Microorganisms (VKPM) FGUP GosNII Genetika (1 Dorozhny proezd, 1 Moscow 117545, Russian Federation) on Jan. 30, 2001 under accession number VKPM B-8066 and then converted to a deposit under the Budapest Treaty on Feb. 1, 2002. The *E. coli* H81 mutants harboring the P$_{tac7}$-yajL cassette were selected on the plates containing LB-medium, agar (1.5%) and chloramphenicol (20 mg/L). Thus the strain *E. coli* H81 P$_{tac7}$-yajL was obtained. Replacement of the promoter region of the yajL gene was verified by PCR as described in Section 1.2 of Example 1.

Example 2

Production of L-Valine by the *E. coli* H81 P$_{tac7}$-yajL Strain

The modified *E. coli* H81 P$_{tac7}$-yajL and the control *E. coli* H81 strains were each cultivated at 32° C. for 18 hours in LB-medium (also referred to as lysogenic broth or Luria-Bertani medium as described in Sambrook, J. and Russell, D. W. "Molecular Cloning: A Laboratory Manual", 3$^{rd}$ ed., Cold Spring Harbor Laboratory Press (2001)). Then, 0.2 mL of the obtained culture was inoculated into 2 mL of a fermentation medium in 20×200-mm test tubes and cultivated at 32° C. for 66 hours on a rotary shaker at 250 rpm to an OD$_{550}$ of ~29 until glucose consumption.

The composition of the fermentation medium (g/L) was as follows:

| | |
|---|---|
| Glucose | 60.0 |
| (NH$_4$)$_2$SO$_4$ | 15.0 |
| KH$_2$PO$_4$ | 1.5 |
| MgSO$_4$•7H$_2$O | 1.0 |
| Thiamine-HCl | 0.1 |
| CaCO$_3$ | 25.0 |
| LB-medium | 10% (v/v) |

The fermentation medium was sterilized at 116° C. for 30 min, except that glucose and CaCO$_3$ were sterilized separately as follows: glucose at 110° C. for 30 min and CaCO$_3$ at 116° C. for 30 min. The pH was adjusted to 7.0 by KOH solution.

After cultivation, accumulated L-valine was measured using thin-layer chromatography (TLC). TLC plates (10×20 cm) were coated with 0.11-mm layers of Sorbfil™ silica gel containing non-fluorescent indicator (Sorbpolymer™, Krasnodar, Russian Federation). Samples were applied onto the plates with the Camag Linomat™ 5 sample applicator. The Sorbfil plates were developed with a mobile phase consisting of propan-2-ol:ethylacetate:25% aqueous ammonia:water (16:16:5:10, v/v). A solution of ninhydrin (2%, w/v) in acetone was used as the visualizing reagent. After development, plates were dried and scanned with the Camag TLC Scanner 3™ in absorbance mode with detection at 520 nm using winCATS™ software (version 1.4.2).

The results of 3 independent test-tube fermentations are shown in Table 1. As it can be seen from the Table 1, the modified *E. coli* H81 P$_{tac7}$-yajL strain was able to accumulate a higher amount of L-valine as compared with the parent *E. coli* H81 strain.

TABLE 1

| Production of L-valine. | |
|---|---|
| Strain | Val, g/L |
| *E. coli* H81 (control) | 9.7 |
| *E. coli* H81 P$_{tac7}$-yajL | 10.7 |

Example 3

Construction of the *E. coli* L-Phenylalanine-Producing Strain Modified to Overexpress the yajL Gene The P$_{tac7}$-yajL fragment was introduced into *E. coli* DV269 (TyrA-LAA) strain, also known as *E. coli* MG1655 htrE:(P$_L$-yddG)[MUDaroG4-pheA$^{fbr}$-aroL], as described in Section 1.3 of Example 1. The *E. coli* MG1655 P$_{tac7}$-yajL strain (see Example 1.1) was used as a donor. Construction of the *E. coli* DV269 (TyrA-LAA) strain is described in Doroshenko V. G. et al., Construction of an L-phenylalanine-producing tyrosine-prototrophic *Escherichia coli* strain using tyrA ssrA-like tagged alleles, *Biotechnol. Lett.,* 2010, 35:1117-1121. The *E. coli* DV269 (TyrA-LAA) mutants harboring the P$_{tac7}$-yajL cassette were selected on the plates containing LB-medium, agar (1.5%) and chloramphenicol (20 mg/L). Thus the strain *E. coli* DV269 (TyrA-LAA) P$_{tac7}$-yajL was obtained.

Example 4

Production of L-Phenylalanine by the *E. coli* DV269 (TyrA-LAA) P$_{tac7}$-yajL Strain The freshly grown cells of L-phenylalanine-producing *E. coli* DV269 (TyrA-LAA) P$_{tac7}$-yajL and control *E. coli* DV269 (TyrA-LAA) strains were taken from L-agar plates in an amount of 10$^8$ CFU/mL (colony-forming unit, CFU), inoculated into 3 mL of LB-medium in 15×150-mm test tubes and cultivated at 34° C. for 3 hours on a rotary shaker at 250 rpm. Then, 0.2 mL of the obtained culture was inoculated into 2 mL of a fermentation medium in 20×200-mm test tubes and cultivated at 34° C. for 30 hours on a rotary shaker at 240 rpm to an OD$_{540}$ of ~6.5-7 until glucose consumption.

The composition of the fermentation medium (g/L) is as follows:

| | |
|---|---|
| Glucose | 50.0 |
| (NH$_4$)$_2$SO$_4$ | 0.6 |
| K$_2$HPO$_4$•3H$_2$O | 0.6 |
| FeSO$_4$•7H$_2$O | 0.01 |
| MnSO$_4$•5H$_2$O | 0.01 |
| Yeast extract | 2.0 |
| CaCO$_3$ | 20.0 |

Glucose was sterilized separately. CaCO$_3$ was dry-heat sterilized at 180° C. for 2 h.

After cultivation, accumulated L-phenylalanine was measured using thin-layer chromatography (TLC). TLC plates (10×20 cm) were coated with 0.11-mm layers of Sorbfil silica gel containing non-fluorescent indicator (Sorbpolymer, Krasnodar, Russian Federation). Samples were applied onto the plates with the Camag Linomat 5 sample applicator. The Sorbfil plates were developed with a mobile phase consisting of propan-2-ol:ethylacetate:25% aqueous ammonia:water (16:16:3:5, v/v). A solution of ninhydrin (1%, w/v) in acetone was used as the visualizing reagent. After development, plates were dried and scanned with the Camag TLC Scanner 3 in absorbance mode with detection at 520 nm using winCATS software (version 1.4.2).

The results of 10 independent test-tube fermentations are shown in Table 2. As it can be seen from the Table 2, the modified E. coli DV269 (TyrA-LAA) P$_{tac7}$-yajL strain was able to accumulate a higher amount of L-phenylalanine as compared with the parent E. coli DV269 (TyrA-LAA) strain.

TABLE 2

Production of L-phenylalanine.

| Strain | Phe, g/L |
|---|---|
| E. coli DV269 (TyrA-LAA) (control) | 3.8 |
| E. coli DV269 (TyrA-LAA) P$_{tac7}$-yajL | 4.1 |

Example 5

Production of L-Arginine by E. coli 382 P$_{tac7}$-yajL Strain

To test the effect of overexpression of the yajL gene on L-arginine production, the DNA-fragments from the chromosome of the above-described E. coli MG1655 P$_{tac7}$-yajL strain are transferred to the arginine-producing E. coli strain 382 by P1-transduction (Miller, J. H. (1972), Experiments in Molecular Genetics, Cold Spring Harbor Lab. Press, Plainview, N.Y.) to obtain the strain 382 P$_{tac7}$-yajL. The strain 382 was deposited in the Russian National Collection of Industrial Microorganisms (VKPM) FGUP GosNII Genetika (1 Dorozhny proezd, 1 Moscow 117545, Russian Federation) on Apr. 10, 2000 under the accession number VKPM B-7926 and then converted to a deposit under the Budapest Treaty on May 18, 2001.

E. coli strains 382 and 382 P$_{tac7}$-yajL are separately cultivated with shaking (220 rpm) at 37° C. for 18 h in 3 mL of nutrient broth, and 0.3 mL of the obtained cultures are inoculated into 2 mL of a fermentation medium in 20×200-mm test tubes and cultivated at 32° C. for 48 h on a rotary shaker (220 rpm).

After the cultivation, the amount of L-arginine which accumulates in the medium is determined by paper chromatography using a mobile phase consisting of butan-1-ol:acetic acid:water=4:1:1 (v/v). A solution of ninhydrin (2%) in acetone is used as a visualizing reagent. A spot containing L-arginine is cut out, L-arginine is eluted with 0.5% water solution of CdCl$_2$, and the amount of L-arginine is estimated spectrophotometrically at 540 nm.

The composition of the fermentation medium (g/L) is as follows:

| | |
|---|---|
| Glucose | 48.0 |
| (NH$_4$)$_2$SO$_4$ | 35.0 |
| KH$_2$PO$_4$ | 2.0 |
| MgSO$_4$•7H$_2$O | 1.0 |
| Thiamine-HCl | 0.0002 |
| Yeast extract | 1.0 |
| L-isoleucine | 0.1 |
| CaCO$_3$ | 5.0 |

Glucose and magnesium sulfate are sterilized separately. CaCO$_3$ is dry-heat sterilized at 180° C. for 2 h. The pH is adjusted to 7.0.

Example 6

Production of L-Cysteine by E. coli JM15(ydeD) P$_{tac7}$-yajL

To test the effect of overexpression of the yajL gene on L-cysteine production, the DNA fragments from the chromosome of the above-described E. coli MG1655 P$_{tac7}$-yajL strain are transferred to the L-cysteine-producing E. coli strain JM15(ydeD) by P1-transduction to obtain the strain JM15(ydeD) P$_{tac7}$-yajL.

E. coli JM15(ydeD) is a derivative of E. coli JM15 (U.S. Pat. No. 6,218,168), which is transformed with DNA having the ydeD gene encoding a membrane protein, and is not involved in a biosynthetic pathway of any L-amino acid (U.S. Pat. No. 5,972,663).

Fermentation conditions and procedure for evaluation of L-cysteine production were described in detail in Example 6 of U.S. Pat. No. 6,218,168.

Example 7

Production of L-Glutamic Acid by E. coli VL334thrC$^+$ P$_{tac7}$-yajL

To test the effect of overexpression of the yajL gene on L-glutamic acid production, the DNA fragments from the chromosome of the above-described E. coli MG1655 P$_{tac7}$-yajL strain are transferred to the E. coli L-glutamate-producing strain VL334thrC$^+$ (EP1172433 A1) by P1-transduction to obtain the strain VL334thrC$^+$ P$_{tac7}$-yajL. The strain VL334thrC$^+$ was deposited in the Russian National Collection of Industrial Microorganisms (VKPM) FGUP GosNII Genetika (1 Dorozhny proezd, 1 Moscow 117545, Russian Federation) on Dec. 6, 2004 under the accession number VKPM B-8961 and then converted to a deposit under the Budapest Treaty on Dec. 8, 2004.

E. coli strains VL334thrC$^+$ and VL334thrC$^+$ P$_{tac7}$-yajL are separately cultivated for 18-24 h at 37° C. on L-agar plates. Then, one loop of the cells is transferred into test tubes containing 2 mL of fermentation medium. Cultivation is carried out at 30° C. for 3 days with shaking.

After the cultivation, the amount of L-glutamic acid which accumulates in the medium is determined by paper chromatography using a mobile phase consisting of butan-1-ol:acetic acid:water=4:1:1 (v/v) with subsequent staining by ninhydrin (1% solution in acetone), elution of the compounds in 50% ethanol with 0.5% CdCl$_2$ and further estimation of L-glutamic acid at 540 nm.

The composition of the fermentation medium (g/L) is as follows:

| | |
|---|---|
| Glucose | 60.0 |
| (NH$_4$)$_2$SO$_4$ | 25.0 |
| KH$_2$PO$_4$ | 2.0 |
| MgSO$_4$•7H$_2$O | 1.0 |
| Thiamine-HCl | 0.1 |
| L-isoleucine | 0.07 |
| CaCO$_3$ | 25.0 |

Glucose and CaCO$_3$ are sterilized separately. The pH is adjusted to 7.2.

Example 8

Production of L-Leucine by E. coli 57 P$_{tac7}$-yajL

To test the effect of overexpression of the yajL gene on L-leucine production, the DNA fragments from the chromosome of the above-described E. coli MG1655 P$_{tac7}$-yajL strain are transferred to the E. coli L-leucine-producing strain 57 (VKPM B-7386, U.S. Pat. No. 6,124,121) by P1-transduction to obtain the strain 57 P$_{tac7}$-yajL. The strain 57 was deposited in the Russian National Collection of Industrial Microorganisms (VKPM) FGUP GosNII Genetika (1 Dorozhny proezd, 1 Moscow 117545, Russian Federation) on May 19, 1997 under the accession number VKPM B-7386.

E. coli strains 57 and 57 P$_{tac7}$-yajL are separately cultivated for 18-24 h at 37° C. on L-agar plates. To obtain a seed culture, the strains are grown on a rotary shaker (250 rpm) at 32° C. for 18 h in 20×200-mm test tubes containing 2 mL of L-broth (Sambrook, J. and Russell, D. W. (2001) "Molecular Cloning: A Laboratory Manual", 3$^{rd}$ ed., Cold Spring Harbor Laboratory Press) supplemented with sucrose (4%). Then, the fermentation medium is inoculated with 0.2 mL of seed material (10%). The fermentation is performed in 2 mL of a minimal fermentation medium in 20×200-mm test tubes. Cells are grown for 48-72 h at 32° C. with shaking at 250 rpm. The amount of L-leucine which accumulates in the medium is determined by paper chromatography using a mobile phase consisting of butan-1-ol:acetic acid:water=4:1:1 (v/v).

The composition of the fermentation medium (g/L) is as follows:

| | |
|---|---|
| Glucose | 60.0 |
| (NH$_4$)$_2$SO$_4$ | 25.0 |
| K$_2$HPO$_4$ | 2.0 |
| MgSO$_4$•7H$_2$O | 1.0 |
| Thiamine-HCl | 0.01 |
| CaCO$_3$ | 25.0 |

Glucose is sterilized separately. CaCO$_3$ is dry-heat sterilized at 180° C. for 2 h. The pH is adjusted to 7.2.

Example 9

Production of L-Lysine by E. coli AJ11442 P$_{tac7}$-yajL

To test the effect of overexpression of the yajL gene on L-lysine production, the DNA fragments from the chromosome of the above-described E. coli MG1655 P$_{tac7}$-yajL strain are transferred to the L-lysine-producing E. coli strain AJ11442 by P1-transduction to obtain the AJ11442 P$_{tac7}$-yajL strain. The strain AJ11442 was deposited in National Institute of Bioscience and Human Technology of Agency of Industrial Science and Technology (currently Incorporated Administrative Agency, National Institute of Technology and Evaluation, International Patent Organism Depositary (NITE-IPOD, #120, 2-5-8 Kazusakamatari, Kisarazu-shi, Chiba-ken 292-0818, JAPAN) on May 1, 1981 under a deposition number of FERM P-5084. Then it was converted to an international deposit under the provisions of the Budapest Treaty on Oct. 29, 1987 and received an accession number of FERM BP-1543. The pCABD2 plasmid includes the dapA gene encoding dihydrodipicolinate synthase having a mutation which desensitizes feedback inhibition by L-lysine, the lysC gene encoding aspartokinase III having a mutation which desensitizes feedback inhibition by L-lysine, the dapB gene encoding dihydrodipicolinate reductase, and the ddh gene encoding diaminopimelate dehydrogenase (U.S. Pat. No. 6,040,160).

E. coli strains AJ11442 and AJ11442 P$_{tac7}$-yajL are separately cultivated in L-medium containing streptomycin (20 mg/L) at 37° C., and 0.3 mL of the obtained culture is inoculated into 20 mL of the fermentation medium containing the required drugs in a 500-mL flask. The cultivation is carried out at 37° C. for 16 h by using a reciprocal shaker at the agitation speed of 115 rpm. After the cultivation, the amounts of L-lysine and residual glucose in the medium are determined by a known method (Biotech-Analyzer™ AS210, Sakura Seiki Co.). Then, the yield of L-lysine is calculated relative to consumed glucose for each of the strains.

The composition of the fermentation medium (g/L) is as follows:

| | |
|---|---|
| Glucose | 40.0 |
| (NH$_4$)$_2$SO$_4$ | 24.0 |
| K$_2$HPO$_4$ | 1.0 |
| MgSO$_4$•7H$_2$O | 1.0 |
| FeSO$_4$•7H$_2$O | 0.01 |
| MnSO$_4$•5H$_2$O | 0.01 |
| Yeast extract | 2.0 |

The pH is adjusted to 7.0 by KOH and the medium is autoclaved at 115° C. for 10 min. Glucose and magnesium sulfate are sterilized separately. CaCO$_3$ is dry-heat sterilized at 180° C. for 2 h and added to the medium for a final concentration of 30 g/L.

Example 10

Production of L-Proline by E. coli 702ilvA P$_{tac7}$-yajL

To test the effect of overexpression of the yajL gene on L-proline production, the DNA fragments from the chromosome of the above-described E. coli MG1655 P$_{tac7}$-yajL strain are transferred to the proline-producing E. coli strain 702ilvA by P1-transduction to obtain the strain 702ilvA P$_{tac7}$-yajL. The strain 702ilvA was deposited in the Russian National Collection of Industrial Microorganisms (VKPM) FGUP GosNII Genetika (1 Dorozhny proezd, 1 Moscow 117545, Russian Federation) on Jul. 18, 2000 under the accession number VKPM B-8012 and then converted to a deposit under the Budapest Treaty on May 18, 2001.

E. coli strains 702ilvA and 702ilvA P$_{tac7}$-yajL are separately cultivated for 18-24 h at 37° C. on L-agar plates. Then, these strains are cultivated under the same conditions as in Example 7 (Production of L-glutamic acid).

Example 11

Production of L-Threonine by *E. coli* B-3996 $P_{tac7}$-yajL

To test the effect of overexpression of the yajL gene on L-threonine production, the DNA fragments from the chromosome of the above-described *E. coli* MG1655 $P_{tac7}$-yajL strain are transferred to the L-threonine-producing *E. coli* strain VKPM B-3996 by P1-transduction to obtain the strain B-3996 $P_{tac7}$-yajL. The strain B-3996 was deposited on Nov. 19, 1987 in the All-Union Scientific Center of Antibiotics (Russian Federation, 117105 Moscow, Nagatinskaya Street, 3-A) under the accession number RIA 1867. The strain was also deposited in the Russian National Collection of Industrial Microorganisms (VKPM) FGUP GosNII Genetika (1 Dorozhny proezd, 1 Moscow 117545, Russian Federation) on Apr. 7, 1987 under the accession number VKPM B-3996.

*E. coli* strains B-3996 and B-3996 $P_{tac7}$-yajL are separately cultivated for 18-24 h at 37° C. on L-agar plates. To obtain a seed culture, the strains are grown on a rotary shaker (250 rpm) at 32° C. for 18 h in 20×200-mm test tubes containing 2 mL of L-broth (Sambrook, J. and Russell, D. W. (2001) "Molecular Cloning: A Laboratory Manual", $3^{rd}$ ed., Cold Spring Harbor Laboratory Press) supplemented with glucose (4%). Then, the fermentation medium is inoculated with 0.2 mL (10%) of seed material. The fermentation is performed in 2 mL of minimal medium in 20×200-mm test tubes. Cells are grown for 65 h at 32° C. with shaking at 250 rpm.

After cultivation, the amount of L-threonine which accumulates in the medium is determined by paper chromatography using a mobile phase consisting of butan-1-ol:acetic acid:water=4:1:1 (v/v). A solution of ninhydrin (2%) in acetone is used as a visualizing reagent. A spot containing L-threonine is cut out, L-threonine is eluted with 0.5% water solution of $CdCl_2$, and the amount of L-threonine is estimated spectrophotometrically at 540 nm.

The composition of the fermentation medium (g/L) is as follows:

| | |
|---|---|
| Glucose | 80.0 |
| $(NH_4)_2SO_4$ | 22.0 |
| NaCl | 0.8 |
| $KH_2PO_4$ | 2.0 |
| $MgSO_4 \cdot 7H_2O$ | 0.8 |
| $FeSO_4 \cdot 7H_2O$ | 0.02 |
| $MnSO_4 \cdot 5H_2O$ | 0.02 |
| Thiamine-HCl | 0.0002 |
| Yeast extract | 1.0 |
| $CaCO_3$ | 30.0 |

Glucose and magnesium sulfate are sterilized separately. $CaCO_3$ is sterilized by dry-heat at 180° C. for 2 h. The pH is adjusted to 7.0. The antibiotic is introduced into the medium after sterilization.

Example 12

Production of L-Tryptophan by *E. coli* SV164(pGH5) $P_{tac7}$-yajL

To test the effect of overexpression of the yajL gene on L-tryptophan production, the DNA fragments from the chromosome of the above-described *E. coli* MG1655 $P_{tac7}$-yajL strain are transferred to the L-tryptophan-producing *E. coli* strain SV164(pGH5) by P1-transduction to obtain the strain SV164(pGH5) $P_{tac7}$-yajL. The strain SV164 has the trpE allele encoding anthranilate synthase free from feedback inhibition by tryptophan. The plasmid pGH5 harbors a mutant serA gene encoding phosphoglycerate dehydrogenase free from feedback inhibition by serine. The strain SV164(pGH5) was described in detail in U.S. Pat. No. 6,180,373 or EP0662143 B1.

*E. coli* strains SV164(pGH5) and SV164(pGH5) $P_{tac7}$-yajL are separately cultivated with shaking at 37° C. for 18 h in 3 mL of nutrient broth supplemented with tetracycline (20 mg/L, marker of pGH5 plasmid). The obtained cultures (0.3 mL each) are inoculated into 3 mL of a fermentation medium containing tetracycline (20 mg/L) in 20×200-mm test tubes, and cultivated at 37° C. for 48 h with a rotary shaker at 250 rpm. After cultivation, the amount of L-tryptophan which accumulates in the medium is determined by TLC. The 10×15-cm TLC plates coated with 0.11-mm layers of Sorbfil silica gel containing non-fluorescent indicator (Stock Company Sorbpolymer, Krasnodar, Russian Federation) are used. The Sorbfil plates are developed with a mobile phase consisting of propan-2-ol:ethylacetate:25% aqueous ammonia:water=40:40:7:16 (v/v). A solution of ninhydrin (2%) in acetone is used as a visualizing reagent. The fermentation medium components are listed in Table 3, but should be sterilized in separate groups (A, B, C, D, E, F, and H), as shown, to avoid adverse interactions during sterilization.

TABLE 3

| Solutions | Component | Final concentration, g/L |
|---|---|---|
| A | $KH_2PO_4$ | 1.5 |
| | NaCl | 0.5 |
| | $(NH_4)_2SO_4$ | 1.5 |
| | L-Methionine | 0.05 |
| | L-Phenylalanine | 0.1 |
| | L-Tyrosine | 0.1 |
| | Mameno* (as the amount of nitrogen) | 0.07 |
| B | Glucose | 40.0 |
| | $MgSO_4 \cdot 7H_2O$ | 0.3 |
| C | $CaCl_2$ | 0.011 |
| D | $FeSO_4 \cdot 7H_2O$ | 0.075 |
| | Sodium citrate | 1.0 |
| E | $Na_2MoO_4 \cdot 2H_2O$ | 0.00015 |
| | $H_3BO_3$ | 0.0025 |
| | $CoCl_2 \cdot 6H_2O$ | 0.00007 |
| | $CuSO_4 \cdot 5H_2O$ | 0.00025 |
| | $MnCl_2 \cdot 4H_2O$ | 0.0016 |
| | $ZnSO_4 \cdot 7H_2O$ | 0.0003 |
| F | Thiamine-HCl | 0.005 |
| G | $CaCO_3$ | 30.0 |
| H | Pyridoxine | 0.03 |

The pH of solution A is adjusted to 7.1 with $NH_4OH$.
*Mameno ™ is the soybean meal hydrolysate (Ajinomoto Co, Inc.).

Example 13

Production of L-Citrulline by *E. coli* 382ΔargG $P_{tac7}$-yajL

To test the effect of overexpression of the yajL gene on L-citrulline production, the DNA fragments from the chromosome of the above-described *E. coli* MG1655 $P_{tac7}$-yajL strain are transferred to the L-citrulline producing *E. coli* strain 382ΔargG by P1-transduction to obtain the strain 382ΔargG P$_{tac7}$-yajL. The strain 382ΔargG is obtained by deletion of argG gene on the chromosome of 382 strain (VKPM B-7926) by the method initially developed by Datsenko K. A. and Wanner B. L. called "λRed/ET-mediated integration" (Datsenko K. A. and Wanner B. L., *Proc. Natl. Acad. Sci. USA*, 2000, 97(12):6640-6645). According to this procedure, the PCR primers homologous to both the region adjacent to the argG gene and the gene which confers antibiotic resistance in the template plasmid are constructed. The plasmid pMW118-λattL-cat-λattR (WO 05/010175) is used as the template in the PCR reaction.

*E. coli* strains 382ΔargG and 382ΔargG P$_{tac7}$-yajL are separately cultivated with shaking at 37° C. for 18 h in 3 mL of nutrient broth, and 0.3 mL of the obtained cultures are inoculated into 2 mL of a fermentation medium in 20×200-mm test tubes and cultivated at 32° C. for 48 h on a rotary shaker.

After the cultivation, the amount of L-citrulline which accumulates in the medium is determined by paper chromatography using a mobile phase consisting of butan-1-ol: acetic acid:water=4:1:1 (v/v). A solution of ninhydrin (2%) in acetone is used as a visualizing reagent. A spot containing citrulline is cut out, L-citrulline is eluted with 0.5% water solution of CdCl$_2$, and the amount of L-citrulline is estimated spectrophotometrically at 540 nm.

The composition of the fermentation medium (g/L) is as follows:

| | |
|---|---|
| Glucose | 48.0 |
| (NH$_4$)$_2$SO$_4$ | 35.0 |
| KH$_2$PO$_4$ | 2.0 |
| MgSO$_4$•7H$_2$O | 1.0 |
| Thiamine-HCl | 0.0002 |
| Yeast extract | 1.0 |
| L-isoleucine | 0.1 |
| L-arginine | 0.1 |
| CaCO$_3$ | 5.0 |

Glucose and magnesium sulfate are sterilized separately. CaCO$_3$ is dry-heat sterilized at 180° C. for 2 h. The pH is adjusted to 7.0.

Example 14

Production of L-Ornithine by *E. coli* 382ΔargFΔargI P$_{tac7}$-yajL

To test the effect of overexpression of the yajL gene on L-ornithine production, the DNA fragments from the chromosome of the above-described *E. coli* MG1655 P$_{tac7}$-yajL strain are transferred to the L-ornithine producing *E. coli* strain 382ΔargFΔargI by P1-transduction to obtain the strain 382ΔargFΔargI P$_{tac7}$-yajL. The strain 382ΔargFΔargI is obtained by consecutive deletion of argF and argI genes on the chromosome of 382 strain (VKPM B-7926) by the method initially developed by Datsenko K. A. and Wanner B. L. called "λRed/ET-mediated integration" (Datsenko K. A. and Wanner B. L., *Proc. Natl. Acad. Sci. USA*, 2000, 97(12):6640-6645). According to this procedure, two pairs of PCR primers homologous to both the region adjacent to the argF or argI gene and the gene which confers antibiotic resistance in the template plasmid are constructed. The plasmid pMW118-λattL-cat-λattR (WO 05/010175) is used as the template in the PCR reaction.

*E. coli* strains 382ΔargFΔargI and 382ΔargFΔargI P$_{tac7}$-yajL are separately cultivated with shaking at 37° C. for 18 h in 3 mL of nutrient broth, and 0.3 mL of the obtained cultures are inoculated into 2 mL of a fermentation medium in 20×200-mm test tubes and cultivated at 32° C. for 48 h on a rotary shaker.

After the cultivation, the amount of ornithine which accumulates in the medium is determined by paper chromatography using a mobile phase consisting of butan-1-ol: acetic acid:water=4:1:1 (v/v). A solution of ninhydrin (2%) in acetone is used as a visualizing reagent. A spot containing ornithine is cut out, ornithine is eluted with 0.5% water solution of CdCl$_2$, and the amount of ornithine is estimated spectrophotometrically at 540 nm.

The composition of the fermentation medium (g/L) is as follows:

| | |
|---|---|
| Glucose | 48.0 |
| (NH$_4$)$_2$SO$_4$ | 35.0 |
| KH$_2$PO$_4$ | 2.0 |
| MgSO$_4$•7H$_2$O | 1.0 |
| Thiamine-HCl | 0.0002 |
| Yeast extract | 1.0 |
| L-isoleucine | 0.1 |
| L-arginine | 0.1 |
| CaCO$_3$ | 5.0 |

Glucose and magnesium sulfate are sterilized separately. CaCO$_3$ is dry-heat sterilized at 180° C. for 2 h. The pH is adjusted to 7.0.

While the invention has been described in detail with reference to preferred embodiments thereof, it will be apparent to one skilled in the art that various changes can be made, and equivalents employed, without departing from the scope of the invention. All the cited references herein are incorporated by reference as a part of this application.

The invention claimed is:

1. A method for producing an L-amino acid comprising:
   (i) cultivating an L-amino acid-producing bacterium of the family Enterobacteriaceae in a culture medium to produce said L-amino acid in the bacterium or the culture medium, or both; and,
   (ii) collecting said L-amino acid from the bacterium or the culture medium, or both, wherein said bacterium has been modified to overexpress the yajL gene.

2. The method according to claim 1, wherein said bacterium belongs to the genus *Escherichia*.

3. The method according to claim 2, wherein said bacterium is *Escherichia coli*.

4. The method according to claim 1, wherein said yajL gene is overexpressed by increasing a copy number of the yajL gene or modifying an expression control sequence of the yajL gene so that the expression of said gene is enhanced as compared to a non-modified bacterium.

5. The method according to claim 1, wherein said L-amino acid is selected from the group consisting of L-phenylalanine, L-tryptophan, L-tyrosine, L-alanine, L-arginine, L-asparagine, L-aspartic acid, L-citrulline, L-cysteine, L-glutamic acid, L-glutamine, glycine, L-histidine, L-isoleucine, L-leucine, L-lysine, L-methionine, L-ornithine, L-proline, L-serine, L-threonine, and L-valine.

6. The method according to claim 5, wherein said L-amino acid is selected from the group consisting of L-alanine, L-isoleucine, L-leucine, L-valine, and L-phenylalanine.

7. The method according to claim 5, wherein said L-amino acid is L-phenylalanine.

8. The method according to claim 5, wherein said L-amino acid is L-valine.

* * * * *

SEQUENCE LISTING

```
<160> NUMBER OF SEQ ID NOS: 9

<210> SEQ ID NO 1
<211> LENGTH: 591
<212> TYPE: DNA
<213> ORGANISM: Escherichia coli
<220> FEATURE:
<221> NAME/KEY: CDS
<222> LOCATION: (1)..(591)

<400> SEQUENCE: 1 atg agc gca tcg gca ctg gtt tgc ctc gcc cct ggt agt gaa gag act      48
Met Ser Ala Ser Ala Leu Val Cys Leu Ala Pro Gly Ser Glu Glu Thr
1               5                   10                  15
```

```
gaa gcc gtc acc act atc gat ctg ctg gtt cgc ggc ggt atc aaa gtc    96
Glu Ala Val Thr Thr Ile Asp Leu Leu Val Arg Gly Gly Ile Lys Val
         20                  25                  30 acc act gcc agc gtc gcc agc gat ggt aac ctg gcg att acc tgc tcg   144
Thr Thr Ala Ser Val Ala Ser Asp Gly Asn Leu Ala Ile Thr Cys Ser
     35                  40                  45 cgc ggc gtg aag ctg ctg gcg gat gcg ccg ctg gtc gaa gtg gct gat   192
Arg Gly Val Lys Leu Leu Ala Asp Ala Pro Leu Val Glu Val Ala Asp
 50                  55                  60 ggc gaa tat gac gtg atc gtg ctg cct ggt ggc att aaa ggc gcg gag   240
Gly Glu Tyr Asp Val Ile Val Leu Pro Gly Gly Ile Lys Gly Ala Glu
 65                  70                  75                  80 tgt ttt cgc gat agc act ctg ctg gtt gaa acc gtt aaa cag ttc cac   288
Cys Phe Arg Asp Ser Thr Leu Leu Val Glu Thr Val Lys Gln Phe His
             85                  90                  95 cgt tcc ggg cgt atc gtc gcg gct att tgc gcc gcg cca gcc acc gtg   336
Arg Ser Gly Arg Ile Val Ala Ala Ile Cys Ala Ala Pro Ala Thr Val
            100                 105                 110 ctg gtg ccg cac gat atc ttc ccg att ggt aat atg acc ggc ttc ccg   384
Leu Val Pro His Asp Ile Phe Pro Ile Gly Asn Met Thr Gly Phe Pro
        115                 120                 125 acg ctg aaa gac aaa att ccc gcc gaa caa tgg ctg gac aag cgc gtc   432
Thr Leu Lys Asp Lys Ile Pro Ala Glu Gln Trp Leu Asp Lys Arg Val
    130                 135                 140 gtc tgg gat gca cgg gta aaa ttg ctg acc agc cag ggg ccg ggt aca   480
Val Trp Asp Ala Arg Val Lys Leu Leu Thr Ser Gln Gly Pro Gly Thr
145                 150                 155                 160 gct atc gac ttt ggt ctg aaa atc atc gac ctg ttg gtt ggg cgt gaa   528
Ala Ile Asp Phe Gly Leu Lys Ile Ile Asp Leu Leu Val Gly Arg Glu
                165                 170                 175 aaa gcc cat gaa gtg gca tca caa ctg gtg atg gcg gca ggg att tat   576
Lys Ala His Glu Val Ala Ser Gln Leu Val Met Ala Ala Gly Ile Tyr
            180                 185                 190 aat tat tac gag tag                                               591
Asn Tyr Tyr Glu
        195
```

<210> SEQ ID NO 2
<211> LENGTH: 196
<212> TYPE: PRT
<213> ORGANISM: Escherichia coli

<400> SEQUENCE: 2

```
Met Ser Ala Ser Ala Leu Val Cys Leu Ala Pro Gly Ser Glu Glu Thr
 1               5                  10                  15

Glu Ala Val Thr Thr Ile Asp Leu Leu Val Arg Gly Gly Ile Lys Val
             20                  25                  30

Thr Thr Ala Ser Val Ala Ser Asp Gly Asn Leu Ala Ile Thr Cys Ser
         35                  40                  45

Arg Gly Val Lys Leu Leu Ala Asp Ala Pro Leu Val Glu Val Ala Asp
     50                  55                  60

Gly Glu Tyr Asp Val Ile Val Leu Pro Gly Gly Ile Lys Gly Ala Glu
 65                  70                  75                  80

Cys Phe Arg Asp Ser Thr Leu Leu Val Glu Thr Val Lys Gln Phe His
             85                  90                  95

Arg Ser Gly Arg Ile Val Ala Ala Ile Cys Ala Ala Pro Ala Thr Val
            100                 105                 110

Leu Val Pro His Asp Ile Phe Pro Ile Gly Asn Met Thr Gly Phe Pro
```

```
            115                 120                 125
Thr Leu Lys Asp Lys Ile Pro Ala Glu Gln Trp Leu Asp Lys Arg Val
    130                 135                 140

Val Trp Asp Ala Arg Val Lys Leu Leu Thr Ser Gln Gly Pro Gly Thr
145                 150                 155                 160

Ala Ile Asp Phe Gly Leu Lys Ile Ile Asp Leu Leu Val Gly Arg Glu
                165                 170                 175

Lys Ala His Glu Val Ala Ser Gln Leu Val Met Ala Ala Gly Ile Tyr
            180                 185                 190

Asn Tyr Tyr Glu
        195

<210> SEQ ID NO 3
<211> LENGTH: 62
<212> TYPE: DNA
<213> ORGANISM: Artificial Sequence
<220> FEATURE:
<223> OTHER INFORMATION: Primer P1

<400> SEQUENCE: 3
tcatattcac tctcctttct ttttaccatt tcaaacgctc acaattccac acattatacg   60
ag                                                                 62

<210> SEQ ID NO 4
<211> LENGTH: 64
<212> TYPE: DNA
<213> ORGANISM: Artificial Sequence
<220> FEATURE:
<223> OTHER INFORMATION: Primer P2

<400> SEQUENCE: 4
ttgaacaccc ggagtggttg cgggtgagga ggaacacgct caagttagta taaaaaagct   60
gaac                                                               64

<210> SEQ ID NO 5
<211> LENGTH: 1768
<212> TYPE: DNA
<213> ORGANISM: Artificial Sequence
<220> FEATURE:
<223> OTHER INFORMATION: DNA-fragment 1

<400> SEQUENCE: 5
ttgaacaccc ggagtggttg cgggtgagga ggaacacgct caagttagta taaaaaagct   60
gaacgagaaa cgtaaaatga tataaatatc aatatattaa attagatttt gcataaaaaa  120
cagactacat aatactgtaa aacacaacat atgcagtcac tatgaatcaa ctacttagat  180
ggtattagtg acctgtaaca gactgcagtg gtcgaaaaaa aaagcccgca ctgtcaggtg  240
cgggcttttt tctgtgttaa gcttcgacga atttctgcca ttcatccgct tattatcact  300
tattcaggcg tagcaccagg cgtttaaggg caccaataac tgcctaaaaa aaattacgcc  360
ccgccctgcc actcatcgca gtactgttgt aattcattaa gcattctgcc gacatggaag  420
ccatcacaga cggcatgatg aacctgaatc gccagcggca tcagcacctt gtcgccttgc  480
gtataatatt tgcccatggt gaaaacgggg gcgaagaagt tgtccatatt ggccacgttt  540
aaatcaaaac tggtgaaact cacccaggga ttggctgaga cgaaaaacat attctcaata  600
aaccctttag ggaaataggc caggttttca ccgtaacacg ccacatcttg cgaatatatg  660
tgtagaaact gccggaaatc gtcgtggtat tcactccaga gcgatgaaaa cgtttcagtt  720
```

```
tgctcatgga aaacggtgta acaagggtga acactatccc atatcaccag ctcaccgtct      780
ttcattgcca tacggaattc cggatgagca ttcatcaggc gggcaagaat gtgaataaag      840
gccggataaa acttgtgctt attttctttt acggtcttta aaaggccgt aatatccagc      900
tgaacggtct ggttataggt acattgagca actgactgaa atgcctcaaa atgttcttta     960
cgatgccatt gggatatatc aacggtggta tatccagtga ttttttttctc cattttagct   1020
tccttagctc ctgaaaatct cggatccggc caagctagct tggctctagc tagagcgccc    1080
ggttgacgct gctagtgtta cctagcgatt tgtatcttac tgcatgttac ttcatgttgt    1140
caatacctgt ttttcgtgcg acttatcagg ctgtctactt atccggagat ccacaggacg    1200
ggtgtggtcg ccatgatcgc gtagtcgata gtggctccaa gtagcgaagc gagcaggact    1260
gggcggcggc caaagcggtc ggacagtgct ccgagaacgg gtgcgcatag aaattgcatc    1320
aacgcatata gcgctagcag cacgccatag tgactggcga tgctgtcgga atggacgata    1380
tcccgcaaga ggcccggcag taccggcata accaagccta tgcctacagc atccagggtg    1440
acggtgccga ggatgacgat gagcgcattg ttagatttca tacacggtgc ctgactgcgt    1500
tagcaattta actgtgataa actaccgcat taaagcttat cgatgataag ctgtcaaaca    1560
tgagaattcg aaatcaaata atgatttat tttgactgat agtgacctgt tcgttgcaac     1620
aaattgataa gcaatgcttt tttataatgc caacttagta taaaaaagca ggcttcaaga    1680
tctcccctgtg gcaaattaat catcggctcg tataatgtgt ggaattgtga gcgtttgaaa   1740
tggtaaaaag aaaggagagt gaatatga                                        1768
```

<210> SEQ ID NO 6
<211> LENGTH: 20
<212> TYPE: DNA
<213> ORGANISM: Artificial Sequence
<220> FEATURE:
<223> OTHER INFORMATION: Primer P3

<400> SEQUENCE: 6
agtcgcaaca gcatgcacaa                                                   20

<210> SEQ ID NO 7
<211> LENGTH: 20
<212> TYPE: DNA
<213> ORGANISM: Artificial Sequence
<220> FEATURE:
<223> OTHER INFORMATION: Primer P4

<400> SEQUENCE: 7
accagtgccg atgcgctcat                                                   20

<210> SEQ ID NO 8
<211> LENGTH: 966
<212> TYPE: DNA
<213> ORGANISM: Artificial Sequence
<220> FEATURE:
<223> OTHER INFORMATION: DNA-fragment 2

<400> SEQUENCE: 8

```
accagtgccg atgcgctcat attcactctc ctttcttttt accatttcaa acaggcgggt       60
gttttccggt acggcaatcc catgcgcgcg ggcgcggcgt aagagaaaac cattgatata      120
gtcgatttca gtgtggcgca gcgcgcggat atcctgcaac atcgacgaga tattttccgc     180
tgtggcatca atcacctgca tcacgtaatc acgcaaatct tctgctgaag tatgatgccc     240
ttcgcgttcg atcaccgccg cgacttcttc gcatatctgc ataatttctt gcggatgatg     300
```

```
acgtaattca ccgttcgggc aattccagat ggcagtcagt ggattaatca cgcagttgac      360
tgccagcttg cgccacagct cggcgcgaat attgttatgc caggcaacgt caggcaacac      420
ggtttgcaaa atatccgcca gataactgta atccccgtcc tgttgccgtg ccgggccaat      480
atgcgtgata ccgtttgcca catgaataat gacattgccg tcgcggcggg ctgcatgggt      540
ggtggtgccc atcagtaatg gctgctgaat gttttgcaac tcttcgatgg tgcccatgcc      600
gttgtgaatt aacagtattg gcgtagttac aggcagtgtg gacgcgaggc ttttgacggc      660
atcggaaacc tgccatgctt tcagcgtcac caggagcaga tcgctggtgg cgagaaaatc      720
gggatcgttg gcggtcagcg attcgttaaa tatcgaacca tctgtctcaa ccagattcac      780
gctacaataa ggttgcggta cgcgcagcca gccctgaact tcatgaccct gtttgcaaag      840
tgctgtaagc cataattgcc ctaaggcacc gcatcccaat acggtaattt tcattgttcc      900
tcctcacccg caaccactcc gggtgttcaa taaggctatc ccttaattgt gcatgctgtt      960
gcgact                                                                 966
```

<210> SEQ ID NO 9
<211> LENGTH: 1820
<212> TYPE: DNA
<213> ORGANISM: Artificial Sequence
<220> FEATURE:
<223> OTHER INFORMATION: DNA-fragment 3

<400> SEQUENCE: 9

```
agtcgcaaca gcatgcacaa ttaagggata gccttattga acacccggag tggttgcggg       60
tgaggaggaa cacgctcaag ttagtataaa aaagctgaac gagaaacgta aaatgatata      120
aatatcaata tattaaatta gattttgcat aaaaaacaga ctacataata ctgtaaaaca      180
caacatatgc agtcactatg aatcaactac ttagatggta ttagtgacct gtaacagact      240
gcagtggtcg aaaaaaaaag cccgcactgt caggtgcggg cttttttctg tgttaagctt      300
cgacgaattt ctgccattca tccgcttatt atcacttatt caggcgtagc accaggcgtt      360
taagggcacc ataactgcc ttaaaaaaat tacgccccgc cctgccactc atcgcagtac      420
tgttgtaatt cattaagcat tctgccgaca tggaagccat cacagacggc atgatgaacc      480
tgaatcgcca gcggcatcag caccttgtcg ccttgcgtat aatatttgcc catggtgaaa      540
acgggggcga agaagttgtc catattggcc acgtttaaat caaaactggt gaaactcacc      600
cagggattgg ctgagacgaa aaacatattc tcaataaacc ctttagggaa ataggccagg      660
ttttcaccgt aacacgccac atcttgcgaa tatatgtgta gaaactgccg gaaatcgtcg      720
tggtattcac tccagagcga tgaaaacgtt tcagtttgct catggaaaac ggtgtaacaa      780
gggtgaacac tatcccatat caccagctca ccgtctttca ttgccatacg gaattccgga      840
tgagcattca tcaggcgggc aagaatgtga ataaaggccg gataaaactt gtgcttattt      900
ttctttacgg tctttaaaaa ggccgtaata tccagctgaa cggtctggtt ataggtacat      960
tgagcaactg actgaaatgc ctcaaaatgt tctttacgat gccattggga tatatcaacg     1020
gtggtatatc cagtgatttt tttctccatt ttagcttcct tagctcctga aaatctcgga     1080
tccggccaag ctagcttggc tctagctaga gcgcccggtt gacgctgcta gtgttaccta     1140
gcgatttgta tcttactgca tgttacttca tgttgtcaat acctgttttt cgtgcgactt     1200
atcaggctgt ctacttatcc ggagatccac aggacgggtg tggtcgccat gatcgcgtag     1260
tcgatagtgg ctccaagtag cgaagcgagc aggactgggc ggcggccaaa gcggtcggac     1320
```

```
agtgctccga gaacgggtgc gcatagaaat tgcatcaacg catatagcgc tagcagcacg    1380
ccatagtgac tggcgatgct gtcggaatgg acgatatccc gcaagaggcc cggcagtacc    1440
ggcataacca agcctatgcc tacagcatcc agggtgacgg tgccgaggat gacgatgagc    1500
gcattgttag atttcataca cggtgcctga ctgcgttagc aatttaactg tgataaacta    1560
ccgcattaaa gcttatcgat gataagctgt caaacatgag aattcgaaat caaataatga    1620 tttattttg actgatagtg acctgttcgt tgcaacaaat tgataagcaa tgctttttta     1680
taatgccaac ttagtataaa aaagcaggct tcaagatctc cctgtggcaa attaatcatc    1740
ggctcgtata atgtgtggaa ttgtgagcgt ttgaaatggt aaaaagaaag gagagtgaat    1800
atgagcgcat cggcactggt                                                1820
```